(12) United States Patent
Wyatt et al.

(10) Patent No.: US 10,174,401 B2
(45) Date of Patent: Jan. 8, 2019

(54) METHODS FOR BINDING AND PRECIPITATING GOLD USING MICROBIAL-DERIVED METALLOPHORES AND THEIR USES

(71) Applicant: McMaster University, Hamilton (CA)

(72) Inventors: Aubrey Morgan Bailey Wyatt, Toronto (CA); Chad Johnston, Hamilton (CA); Nathan Magarvey, Oakville (CA)

(73) Assignee: McMaster University, Hamilton (CA)

( * ) Notice: Subject to any disclaimer, the term of this patent is extended or adjusted under 35 U.S.C. 154(b) by 309 days.

(21) Appl. No.: 14/760,527

(22) PCT Filed: Jan. 14, 2014

(86) PCT No.: PCT/CA2014/050021
§ 371 (c)(1),
(2) Date: Jul. 13, 2015

(87) PCT Pub. No.: WO2014/107814
PCT Pub. Date: Jul. 17, 2014

(65) Prior Publication Data
US 2015/0354024 A1   Dec. 10, 2015

Related U.S. Application Data

(60) Provisional application No. 61/751,984, filed on Jan. 14, 2013, provisional application No. 61/821,333, (Continued)

(51) Int. Cl.
*C22B 3/18* (2006.01)
*C07K 7/54* (2006.01)
(Continued)

(52) U.S. Cl.
CPC .............. *C22B 3/18* (2013.01); *B22F 9/24* (2013.01); *C07K 7/02* (2013.01); *C07K 7/06* (2013.01); *C07K 7/54* (2013.01); *C12P 21/02* (2013.01); *C22B 11/04* (2013.01); *B22F 1/0018* (2013.01); *B82Y 30/00* (2013.01); *C12N 15/52* (2013.01); *Y02P 10/234* (2015.11)

(58) Field of Classification Search
None
See application file for complete search history.

(56) References Cited

U.S. PATENT DOCUMENTS

2009/0100969 A1* 4/2009 Rosi .................. B22F 1/0018
75/746
2012/0276615 A1 11/2012 Pfeiffer Seeger et al.

OTHER PUBLICATIONS

Lengke, et al. Geochimica et Cosmochimica Acta, 2006, 70, 3646-3661. (Year: 2006).*

(Continued)

*Primary Examiner* — Clare M Perrin
(74) *Attorney, Agent, or Firm* — Bereskin & Parr LLP/S.E.N.C.R.L., s.r.l.; Patricia Folkins

(57) ABSTRACT

The present application discloses metallophores that complex soluble gold and generate solid gold forms, including gold nanoparticles. In an embodiment, the metallophores are microbial metabolites isolated from organisms that are resistant to gold, or are analogs thereof. Methods of using the metallophores to extract and detect gold, along with detectors comprising the metallophores are disclosed.

19 Claims, 25 Drawing Sheets

Related U.S. Application Data filed on May 9, 2013, provisional application No. 61/830,762, filed on Jun. 4, 2013.

(51) Int. Cl.
| | |
|---|---|
| *C12P 21/02* | (2006.01) |
| *C22B 3/00* | (2006.01) |
| *B22F 9/24* | (2006.01) |
| *C07K 7/06* | (2006.01) |
| *C07K 7/02* | (2006.01) |
| *B22F 1/00* | (2006.01) |
| *C12N 15/52* | (2006.01) |
| *B82Y 30/00* | (2011.01) |

(56) References Cited

OTHER PUBLICATIONS

Lengke, et al. Geochimica et Cosmochimica Acta, 2005, 69, 3759-3772. (Year: 2005).*
Reith et al. Geology, 2010, 38, 843-846. (Year: 2010).*
Van Houdt, et al. Antonie van Leeuwenhoek, 2009, 96, 205-226. (Year: 2009).*
International Search Report and Written Opinion of corresponding international application No. PCT/CA2014/050021 dated May 14, 2015.
Johnston, Chad W., et al., "Gold biomineralization by a metallophore from a gold-associated microbe", Nature Chemical Biology, vol. 9, Apr. 2013, 241-245.
Gadd, Geoffrey Michael, "Metals, minerals and microbes: geomicrobiology and bioremediation" Microbiology, vol. 156, 2010, 609-643.
Fairbrother, L., et al, "Biomineralization of Gold in Biofilms of Cupriavidus metallidurans", Environ. Sci. Tech., vol. 47, 2013, 2628-2635.
Reith, F., et al., "Mechanisms of gold biomineralization in the bacterium Cupriavidus Metallidurans" PNAS, Oct. 20, 2009, vol. 106, No. 42, 17757-17762.
Reith, F. et al., "The Geomicrobiology of Gold", The ISME Journal (2007), vol. 1, 567-584.
Husseiny, M.l., et al,. "Biosynthesis of gold nanoparticles using Pseudomonas aeruginosa", Spectorchimica Acta Part A. Mol. Biomol. Spectrosc. 2007 (2007), vol. 67, 1003-1006.
Lengke, M., et al., "Biosynthesis of Gold Nanoparticles: A Review", Met. Nanopart Microbiol, 2011, 37-74.
Malhotra, A., et al., "Biosynthesis of gold and silver nanoparticles using a novel marine strain of Stenotrophomonas", 2013, Biores. Technol., 142, 727-731.
Reith, F., et al. "Biomineralization of Gold: Biofilms on Bacterioform Gold", Science, vol. 313, Jul. 14, 2006, 233-236.

* cited by examiner

METHODS FOR BINDING AND PRECIPITATING GOLD USING MICROBIAL-DERIVED METALLOPHORES AND THEIR USES

RELATED APPLICATIONS

The present application is a National Stage of co-pending International Application No. PCT/CA2014/050021 filed Jan. 14, 2014, which claims the benefit of priority from U.S. provisional patent application No. 61/751,984, filed on Jan. 14, 2013, U.S. provisional patent application No. 61/821,333, filed on May 9, 2013, and U.S. provisional patent application No. 61/830,762, filed on Jun. 4, 2013, the contents of each of which is incorporated by reference in their entirety.

FIELD

The present disclosure relates to methods for detecting gold, extracting soluble gold out of solution and/or forming gold nanoparticles using metal-chelating microbial metabolites. Also included are several novel microbial metabolites that are useful, for example, in the methods of the application.

BACKGROUND

Microorganisms inhabit nearly all surfaces on the planet, an achievement typically attributed to their metabolic versatility. Frequently, secondary metabolic pathways and secreted products of these specialized branches of metabolism are complicit in an organism's ability to capture niches, enhance fitness, and overcome environmental stress and often have significant industrial importance (Vining, 1990). Metals represent an interesting environmental condition for microbes, as some are required for growth (e.g. $Fe^{3+}$) while others inhibit it (e.g. $Au^{3+}$, $Ag^+$, $Hg^+$) (Nies, 1999). Bacterial biofilms exist on the surface of gold nuggets (Reith et al., 2006 & Reith et al., 2010) though soluble gold is inherently toxic (Nies, 1999), these bacteria are implicated in its accumulation and deposition (Reith et al., 2007; Reith et al., 2009). The existence of bacterial biofilms coating gold nuggets and discovery of bacterioform gold suggests that bacteria and specialized bacterial metabolic processes are involved in gold biomineralization (Reith et al., 2006; Reith et al., 2010; Reith et al., 2009; Reith et al., 2007). Sequencing gold nugget microbiota has revealed *Cupriavidus metallidurans* and *Delftia acidovorans* are dominant organisms within such communities and comprise over 90% of these populations (Reith et al., 2010). Investigations into *C. metallidurans* have revealed that it bioaccumulates inert gold nanoparticles within its cytoplasm, as a mechanism to protect itself from soluble gold (Reith et al., 2009).

SUMMARY

Disclosed herein are methods of chelating soluble gold ions, resulting in the formation of solid gold, such as gold nanoparticles, using gold-chelating microbial metabolites, such as non-ribosomal peptides. Also disclosed herein are novel microbial metabolites, and analogs thereof, that facilitate chelation of gold ions ($Au^{3+}$) and deposition of solid gold ($Au^0$).

Accordingly, the present application includes a method of removing soluble gold in a sample comprising:
(a) contacting the sample with a metallophore under conditions to form a complex between the soluble gold and the metallophore and conversion of the soluble gold into solid gold; and
(b) isolating the solid gold from the sample,
wherein the metallophore is a microbial metabolite comprising a chelation core that binds to gold ions and wherein the microbial metabolite converts the soluble gold ions to solid gold ($Au^0$).

In an embodiment the solid gold that is formed comprises gold nanoparticles according, the present application further includes a method of forming gold nanoparticles comprising:
(a) contacting a sample comprising soluble gold with a metallophore under conditions to form a complex between the soluble gold and the metallophore and conversion of the soluble gold into gold nanoparticles; and
(b) isolating the gold nanoparticles from the sample,
wherein the metallophore is a microbial metabolite comprising a chelation core that binds to gold ions and wherein the microbial metabolite converts the soluble gold ions to solid gold ($Au^0$).

In a further embodiment, the present application also includes a method for detecting the presence of soluble gold in a sample comprising:
(a) contacting a sample suspected of comprising soluble gold with a metallophore under conditions to form a complex between the soluble gold and the metallophore and conversion of the soluble gold into solid gold; and
(b) observing the sample for the presence of solid gold,
wherein the metallophore is a microbial metabolite comprising a chelation core that binds to gold ions and wherein the microbial metabolite converts the soluble gold ions to solid gold ($Au^0$).

In an embodiment, the metallophore is a metabolite isolated from microbial strains that exist and grow in the presence of soluble gold. In an embodiment, the microbial strains biomineralize the gold producing solid gold, such as gold nanoparticles. Though the biomineralization process, the microbes are protected from the effects of toxic soluble gold.

In a further embodiment of the present application the metallophore is a bacterial metabolite isolated from bacteria comprising a nucleic acid sequence encoding non-ribosomal peptide synthetase (NRPS) operons such as those shown in FIG. 19.

In an embodiment, the bacteria are from the genera, *Delftia*, *Acidovorax* or *Variovorax*. In particular from *D. acidovorans*, *A. citrulli*, or *V. paradoxus*. In a further embodiment, the metabolite is at least partially secreted by the bacteria into its surrounding environment.

In a further embodiment, the metallophore is a compound of the Formula I:

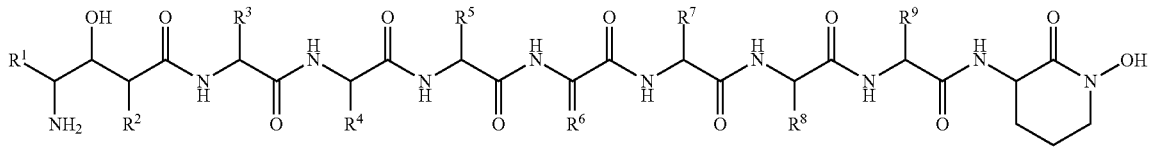

(I)

wherein
R¹ is selected from H and $C_{1-6}$alkyl;
R² is selected from H and $C_{1-6}$alkyl;
R³ is $(CH_2)_nC(O)OH$, unsubstituted or substituted with OH;
R⁴ is selected from $C_{1-6}$alkyl substituted with OH;
R⁵ is selected from H and $C_{1-6}$alkyl;
R⁶ is selected from $CH_2$, $C(C_{1-6}alkyl)(C_{1-6}alkyl)$ and $CHC_{1-6}alkyl$;
R⁷ is

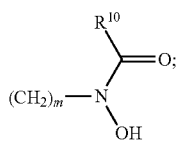

R⁸ is selected from $C_{1-6}$alkyl substituted with OH;
R⁹ is

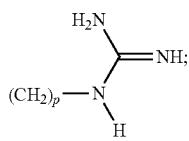

R¹⁰ is selected from H and $C_{1-6}$alkyl; and
n, m and p are independently selected from 1, 2, 3 and 4, or a salt thereof.

In a further embodiment, the metallophore is a compound of the Formula II:

(II)

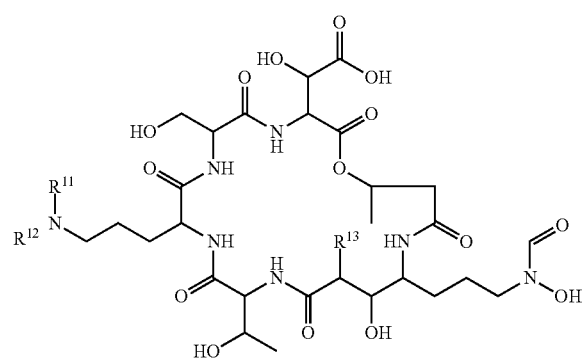

wherein
R¹¹ and R¹² are independently selected from H, OH and C=O;
R¹³ is selected from H and $C_{1-4}$alkyl; or
a salt thereof.

In a further embodiment, the metallophore is a compound of the Formula III:

(III)

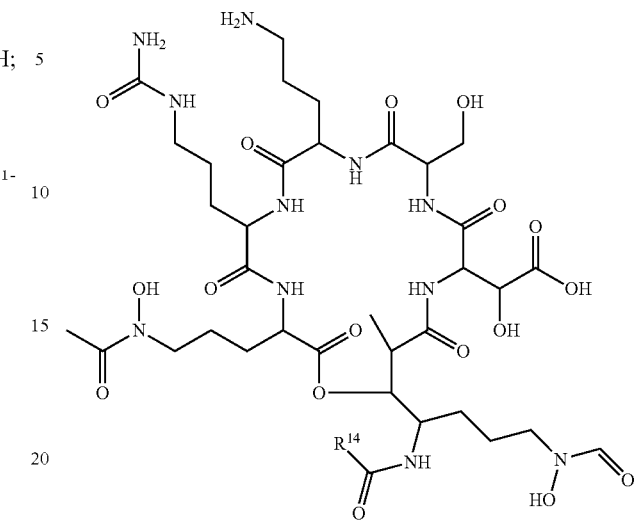

wherein:
R¹⁴ is selected from $C_{1-20}$alkyl and $C_{2-20}$alkenyl; or
a salt thereof.

The present application also includes an isolated compound of the Formula (I), (II) or (III), or a salt thereof.

The present application also includes a detector for gold comprising a carrier and one or more metallophores, wherein the one or more metallophores are microbial metabolites comprising a chelation core that binds to gold ions and wherein the microbial metabolite converts the soluble gold ions to solid gold ($Au^0$). In an embodiment, the one or more metallophores are one or more of the compounds of the Formula I, II or III, or a salt thereof.

Other features and advantages of the present disclosure will become apparent from the following detailed description. It should be understood, however, that the scope of the claims should not be limited by the embodiments set forth in the examples, but should be given the broadest interpretation consistent with the description as a whole.

BRIEF DESCRIPTION OF THE DRAWINGS

The disclosure will now be described in relation to the drawings in which.

DETAILED DESCRIPTION

(I) Definitions

Figure 1:
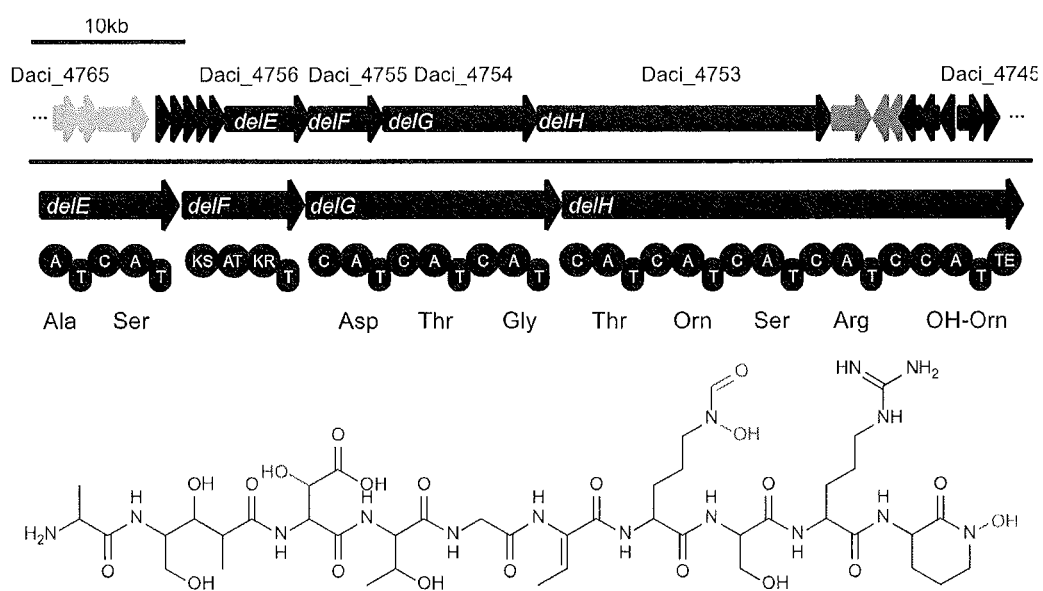
FIG. 1 shows the del gene cluster and domain architecture of NRPS-PKS hybrid assembly-line consisting of adenylation (A), thiolation (T), condensation, (C), ketosynthase (KS), acyltransferase (AT), ketoreductase (KR), and thioesterase domains. Flanking genes for heavy metal resistance (left) and iron metabolism (right) are shown. Predicted activated amino acids are indicated below their respective A domains (Table 1). The final predicted structure of the unknown del metabolite is shown.

Unless otherwise indicated, the definitions and embodiments described in this and other sections are intended to be applicable to all embodiments and aspects of the disclosure herein described for which they are suitable as would be understood by a person skilled in the art.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise. For example, an embodiment including "a metallophore" should be understood to present certain aspects with one metallophore or two or more additional metallophores.

In embodiments comprising an "additional" or "second" component, such as an additional or second metallophore, the second component as used herein is chemically different from the other components or first component. A "third" component is different from the other, first, and second components, and further enumerated or "additional" components are similarly different.

In embodiments of the present application, the compounds described herein have at least one asymmetric center. Where compounds possess more than one asymmetric center, they may exist as diastereomers. It is to be understood that all such isomers and mixtures thereof in any proportion are encompassed within the scope of the present application. It is to be further understood that while the stereochemistry of the compounds may be as shown in any given compound listed herein, such compounds may also contain certain amounts (for example, less than 20%, suitably less than 10%, more suitably less than 5%) of compounds of the present application having alternate stereochemistry. It is intended that any optical isomers, as separated, pure or partially purified optical isomers or racemic mixtures thereof are included within the scope of the present application.

The term "alkyl" as used herein, whether it is used alone or as part of another group, means straight or branched chain, saturated alkyl groups. The term $C_{1-6}$ alkyl means an alkyl group having 1, 2, 3, 4, 5 or 6 carbon atoms.

The term "alkenyl" as used herein means straight or branched chain, unsaturated alkyl groups, that is, a saturated carbon chain that contains one or more, for example one to three, one to two or one, double bond. The term $C_{2-6}$alkenylene means an alkylene group having 2, 3, 4, 5 or 6 carbon atoms.

The term "salt" as used herein means an acid addition salt or a basic addition salt. The formation of a desired compound salt is achieved using standard techniques. For example, the neutral compound is treated with an acid or base in a suitable solvent and the formed salt is isolated by filtration, extraction or any other suitable method.

The term "metallophore" as used herein refers a compound that binds to or chelates metals.

The term "chelation core" as used herein refers to the groups in a metallophore that bind to a metal through the formation of two or more separate coordination bonds. A "coordination bond" is a 2-center, 2-electron bond in which the two electrons derive from the same atom.

The term "chelating amino acid" as used herein refers to an amino acid comprising a side chain with at least one chelating atom (i.e. an atom that has 2 electrons available for formation of a coordination bond). Such amino acids are those comprising at least one heteroatom in the side chain wherein the heteroatom as two electrons available for formation of a chelation bond. In an embodiment, the heteroatom is selected from, O, S and N.

The term "formylated" as used herein refers to functionalization of a compound with a formyl (C(O)H) group. For example, reference to an N-formulated amino acid refers to peptide amino acid (ribosomal or non-ribosomal) in which a side-chain amino functionality has been formulated.

The term "hydroxylated" as used herein refers to functionalization of a compound with a hydroxy (OH) group. For example, reference to an N-hydroxylated amino acid refers to peptide amino acid (ribosomal or non-ribosomal) in which a side-chain amino functionality has been hydroxylated.

The term "acetylated" as used herein refers to functionalization of a compound with a acetyl (C(O)CH$_3$) group. For example, reference to an N-acetylated amino acid refers to peptide amino acid (ribosomal or non-ribosomal) in which a side-chain amino functionality has been acetylated.

The term "alkylated" as used herein refers to functionalization of a compound with a $C_{1-6}$alkyl group. For example, reference to an N-alkylated amino acid refers to peptide amino acid (ribosomal or non-ribosomal) in which a side-chain amino functionality has been alkylated.

The term "ornithine lactam" as used herein refers to the amino acid:

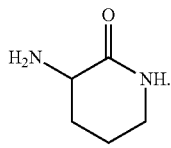

The term "N-hydroxyornithine lactam" as used herein refers to the amino acid:

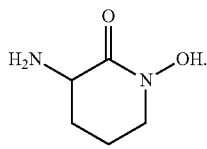

The term "β-hydroxyaspartic acid" refers to the amino acid:

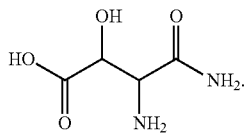

The term "catechol" as used herein refers to a compound comprising a 1,2-dihydroxybenzene group.

The term "isolated" as used herein refers to a compound that is substantially separated from other components which naturally accompany a native compound, such as other bacterial cellular components for an isolated bacterial metabolite.

The term "non-ribosomal peptide" as used herein refers to a class of peptide secondary metabolites usually produced by microorganisms such as bacteria and fungi. Non-ribosomal peptides are synthesized by non-ribosomal peptide synthetases, which, unlike the ribosomes, are independent of messenger RNA. Each non-ribosomal peptide synthetase can synthesize only one type of peptide. Non-ribosomal peptides can have a linear, cyclic and/or branched structure, can contain non-proteinogenic amino acids, including D-amino acids, carry modifications like N-methyl and N-formyl groups, or are glycosylated, acetylated halogenated or hydroxylated. Cyclization of amino acids against the peptide "backbone" is often performed, resulting in oxazolines and thiazolines, and these can be further oxidized or reduced. On occasion, dehydration is performed on serines, resulting in dehydroalanine. There are many other manipulations and variations that non-ribosomal peptides can comprise, for example polyketide extensions. Non-ribosomal peptides can be dimers or trimers of identical sequences chained together or cyclized, or even branched (II) Methods of the Application Delftibactin A and B, and analogs thereof, show considerable promise in the bio-remediation of toxic soluble gold as well as in the detection of the presence of gold in a sample. For example, the reduced nanoparticles formed by delftibactin A are—like delftibactin A itself—nontoxic, and are formed as part of a complex matrix, that would involve considerably less liquid handling. Further, many commercially available methods for removing soluble gold, including the use of activated carbon or ionic-exchange resins, are non-specific, and may result in enrichment for other contaminating metals. Delftibactin A is specific for a small set of metal ions including iron, gallium, and most notably gold, and would be a considerable improvement on currently available methods of remediation.

Accordingly, the present application includes a method of removing soluble gold in a sample comprising:
(a) contacting the sample with a metallophore under conditions to form a complex between the soluble gold and the metallophore and conversion of the soluble gold into solid gold; and
(b) isolating the solid gold from the sample,
wherein the metallophore is a bacterial metabolite comprising a chelation core that binds to gold ions and wherein the bacterial metabolite converts the soluble gold ions to solid gold (Au$^0$).

In an embodiment the solid gold that is formed comprises gold nanoparticles, accordingly the present application further includes a method of forming gold nanoparticles comprising:
(a) contacting a sample comprising soluble gold with a metallophore under conditions to form a complex between the soluble gold and the metallophore and conversion of the soluble gold into gold nanoparticles; and
(b) isolating the gold nanoparticles from the sample,
wherein the metallophore is a bacterial metabolite comprising a chelation core that binds to gold ions and wherein the bacterial metabolite converts the soluble gold ions to solid gold (Au$^0$).

In a further embodiment, the present application also includes a method for detecting the presence of soluble gold in a sample comprising:
(a) contacting a sample suspected of comprising soluble gold with a metallophore under conditions to form a complex between the soluble gold and the metallophore and conversion of the soluble gold into solid gold; and (b) observing the sample for the presence of solid gold, wherein the metallophore is a bacterial metabolite comprising a chelation core that binds to gold ions and wherein the bacterial metabolite converts the soluble gold ions to solid gold ($Au^0$).

In an embodiment of the application, the microbial metabolite comprises at least two to four, or at least, three chelating amino acids. In a further embodiment, the chelating amino acids are selected from:

ornithine and N-formylated, N-acetylated, N-alkylated and N-hydroxylated ornithine;
ornithine lactam and N-formylated, N-acetylated, N-alkylated and N-hydroxylated ornithine lactam;
serine and O-formylated, O-acetylated and O-alkylated serine;
threonine and O-formylated, O-acetylated and O-alkylated threonine;
cysteine and S-formylated, S-acetylated and S-alkylated cysteine;
methionine and S-formylated, S-acetylated and S-alkylated methionine;
β-hydroxyaspartic acid and O-formylated, O-acetylated and O-alkylated β-hydroxyaspartic acid;
histidine and N-formylated, N-acetylated, N-alkylated and N-hydroxylated histidine;
arginine and N-formylated, N-acetylated, N-alkylated and N-hydroxylated arginine;
glutamic acid;
asparagine;
tyrosine;
aspartic acid; and
glutamine.

In a further embodiment, the chelation core comprises a catechol or any other known microbial-derived chelation moiety from a metallophore that has selectivity for gold ions or is used in a process to selectively detect gold ions.

In an embodiment of the application the chelation core of the bacterial metabolite comprises at least two or more, for example, at least two to four, or at least three, chelating amino acids selected from:

ornithine and N-formylated, N-acetylated, N-alkylated and N-hydroxylated ornithine;
ornithine lactam and N-formylated, N-acetylated, N-alkylated and N-hydroxylated ornithine lactam;
serine and O-formylated, O-acetylated and O-alkylated serine;
threonine and O-formylated, O-acetylated and O-alkylated threonine; and
β-hydroxyaspartic acid and O-formylated, O-acetylated and O-alkylated β-hydroxyaspartic acid.

In an embodiment of the application, the metallophore is a non-ribosomal peptide comprising at least one N-formylated hydroxyl ornithine and optionally one or more other chemical moieties selected from N-formylated, N-acetylated, N-alkylated and N-hydroxylated ornithine; ornithine lactam and N-formylated, N-acetylated, N-alkylated and N-hydroxylated ornithine lactam; serine and O-formylated, O-acetylated and O-alkylated serine; threonine and O-formylated, O-acetylated and O-alkylated threonine and β-hydroxy aspartic acid.

In an embodiment of the application, the metallophore is a non-ribosomal peptide comprising 4 to 20 amino acids. In a further embodiment, the metallophore is a non-ribosomal peptide comprising 5 to 15 amino acids. In a further embodiment, the metallophore is a non-ribosomal peptide comprising 6 to 10 amino acids. In another embodiment, the metallophore is a linear non-ribosomal peptide. In another embodiment, the metallophore is a cyclic non-ribosomal peptide.

In an embodiment of the application, the metallophore is a bacterial metabolite. In another embodiment, the bacterial metabolite is isolated from bacterial strains that exist and grow in the presence of soluble gold. In an embodiment, the bacterial strains biomineralize the gold producing solid gold, such as gold nanoparticles. Though the biomineralization process, the bacteria are protected from the effects of toxic soluble gold. In an embodiment, the bacteria are from the genera, *Delftia, Acidovorax* or *Variovorax*. In particular from *D. acidovorans, A. citrulli*, or *V. paradoxus*. In a further embodiment, the metabolite is at least partially secreted by the bacteria into its surrounding environment.

Figure 19:
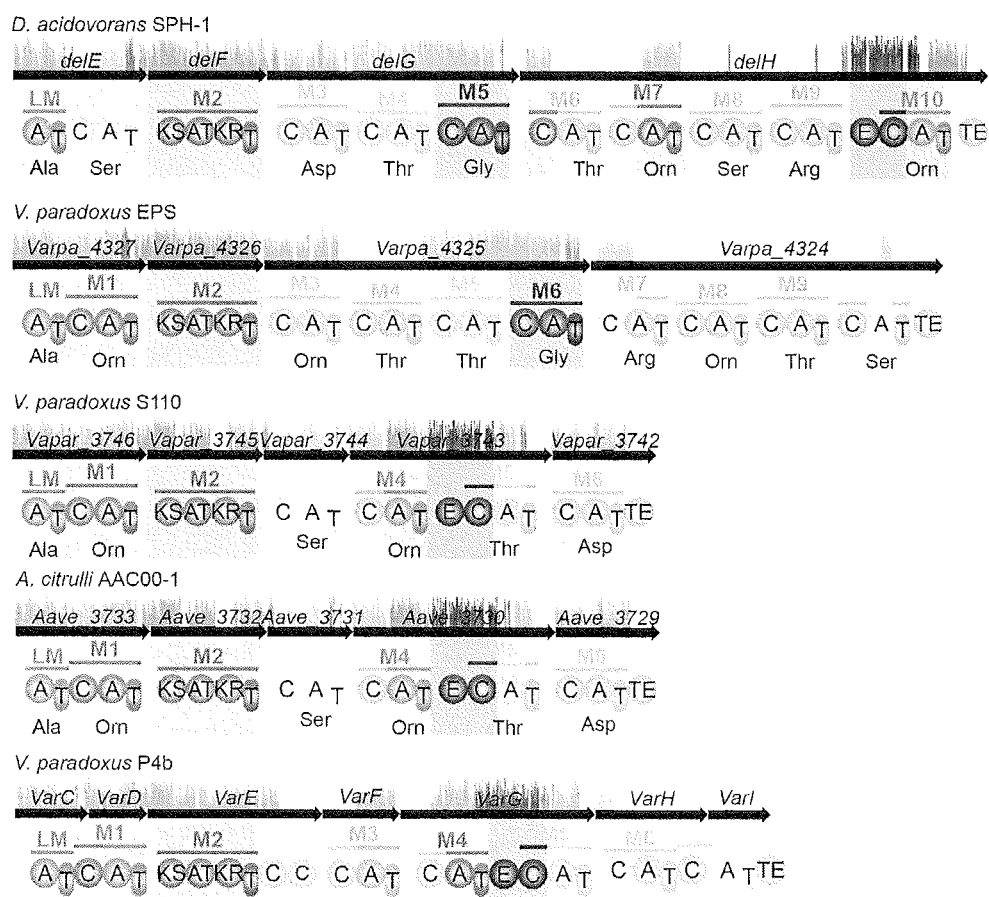
FIG. 19 is a schematic showing the genetic relationship between delftibactin A and related metabolites. The biosynthetic clusters were identified by BLAST searching using the delftibactin A biosynthesis gene cluster as the query. Bars represent nucleotide similarity using a MAUVE analysis. The resulting structures from each gene cluster are shown on the left.

In an embodiment of the present application metallophore is a bacterial metabolite isolated from a bacteria comprising a nucleic acid sequence encoding non-ribosomal peptide synthetase (NRPS) operons such as those shown in FIG. 19. Accordingly, the NRPS operons comprise from initiation to termination ends:

A-T-C-A-T-KS-AT-KR-T-[$Var^1$]-C-A-T-C-A-T-[$Var^2$]-C-A-T-C-A-T-[C-A-T]$_{0-3}$-[E-C-A-T]$_{0-1}$-TE, wherein:
A is a adenylation domain;
T is a thiolation domain;
C is a condensation domain;
KS is a β-ketoacyl synthetase domain;
AT is an acyl transferase domain;
KR is a ketoreductase domain;
E is an epimerase domain;
TE is a termination domain;
$Var^1$ is a direct bond or C; and
$Var^2$ is a direct bond or E.

In further embodiment of the application the metallophore is a compound of Formula I:

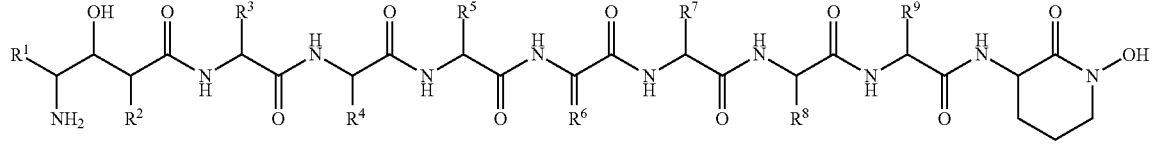

(I)

wherein
$R^1$ is selected from H and $C_{1-6}$alkyl;
$R^2$ is selected from H and $C_{1-6}$alkyl;
$R^3$ is $(CH_2)_nC(O)OH$, unsubstituted or substituted with OH;
$R^4$ is selected from $C_{1-6}$alkyl substituted with OH;
$R^5$ is selected from H and $C_{1-6}$alkyl;

R⁶ is selected from CH₂, C(C₁₋₆alkyl)(C₁₋₆alkyl) and CHC₁₋₆alkyl;
R⁷ is

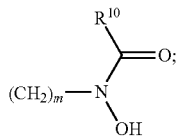

R⁸ is selected from C₁₋₆alkyl substituted with OH;
R⁹ is

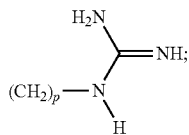

R¹⁰ is selected from H and C₁₋₆alkyl; and
n, m and p are independently selected from 1, 2, 3 and 4, or a salt thereof.

In an embodiment, R¹ is selected from CH₃ and CH₂CH₃. In a further embodiment R¹ is CH₃.

In an embodiment, R² is selected from CH₃ and CH₂CH₃. In a further embodiment R² is CH₃.

In an embodiment, R³ is (CH₂)ₙC(O)OH substituted with OH. In a further embodiment, n is 1.

In an embodiment, R⁴ is selected from C₁₋₄alkyl substituted with OH. In another embodiment, R⁴ is CH(OH)CH₃.

In an embodiment, R⁵ is selected from H and CH₃. In another embodiment, R⁵ is H.

In an embodiment R⁶ is selected from CH₂, CHCH₃ and CHCH₂CH₃.

In an embodiment, R⁷ is

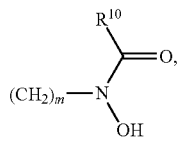

wherein m is 2 or 3 and R¹⁰ is selected from H and CH₃. In a further embodiment, m is 3 and R¹⁰ is H.

In an embodiment, R⁸ is selected from C₁₋₂alkyl substituted with OH. In a further embodiment, R⁸ CH₂OH.

In an embodiment R⁹ is

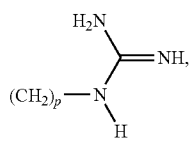

wherein p is 3 or 4. In an embodiment, p is 3.

In an embodiment the metallophore is delftibactin A:

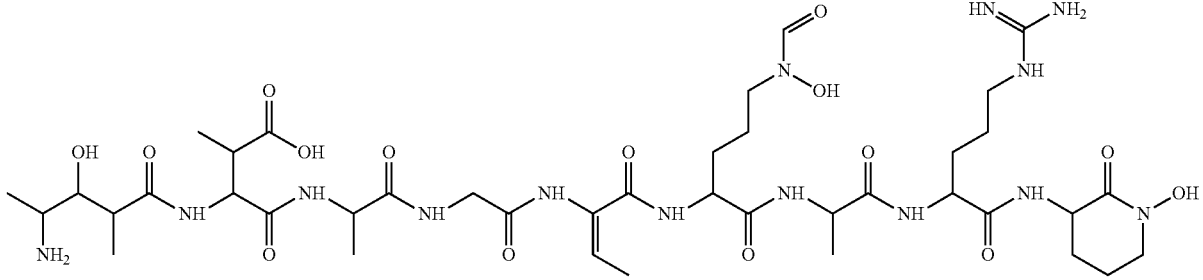 [SMILES: C/C=C(/NC(=O)CNC(=O)C(C)NC(=O)C(NC(=O)C(C)C(O)C(C)N)C(C)C(=O)O)C(=O)NC(CCCN(O)C=O)C(=O)NC(C)C(=O)NC(CCCNC(=N)N)C(=O)NC1CCCN(O)C1=O]

or delftibactin B:

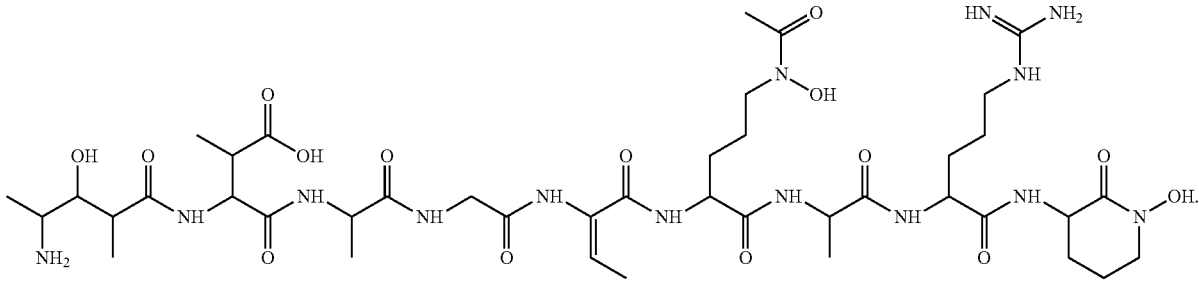 [SMILES: C/C=C(/NC(=O)CNC(=O)C(C)NC(=O)C(NC(=O)C(C)C(O)C(C)N)C(C)C(=O)O)C(=O)NC(CCCN(O)C(C)=O)C(=O)NC(C)C(=O)NC(CCCNC(=N)N)C(=O)NC1CCCN(O)C1=O]

In a further embodiment, the metallophore is delftibactin A. Compared to citrate—the industrially used agent for creating gold nanoparticles—delftibactin A does not need to be heated with the gold-containing sample to form solid gold. Further, the time frame in which the soluble gold is reduced and coalesced as nanoparticles is much faster. Delftibactin, and analogs thereof, also show considerable promise in the bio-remediation of toxic soluble gold, as the reduced nanoparticles formed by delftibactin A are—like delftibactin A itself—nontoxic, and are formed as part of a complex matrix, that would involve considerably less liquid handling. Further, many commercially available methods for removing soluble gold, including the use of activated carbon or ionic-exchange resins, are non-specific, and may result in enrichment for other contaminating metals. Delftibactin A is specific for a small set of metal ions including iron, gallium, and most notably gold, and would be a considerable improvement on currently available methods of remediation.

In yet another embodiment, the metallophore is an analog of delftibactin A which has gold complexing and solid gold forming ability. In a further embodiment, analogs of delftibactin A are those comprising similar gene clusters to the genes that encode the enzymes (non-ribosomal peptide synthetases or NRPS) for producing delftibactin A. For example, the genes that encode the enzymes for producing delftibactin A are used as the query in a BLAST search to identify similar gene clusters in other organisms.

In yet another embodiment, confirmation that a compound isolated from another organism is an analog of delftibactin A is made by comparing the mass spectral (MS) fragmentation pattern of the analog with that of delftibactin. If the analog possesses a similar MS fragmentation pattern to the MS fragmentation pattern of delftibactin then it is likely an analog of delftibactin. In an embodiment, the significance of a match in fragmentation patterns, indicating analogous structures is calculated using computational means, for example as described in Applicant's co-pending PCT Application Publication No. WO 2013/181758.

In a further embodiment, the metallophore is a compound of the Formula II:

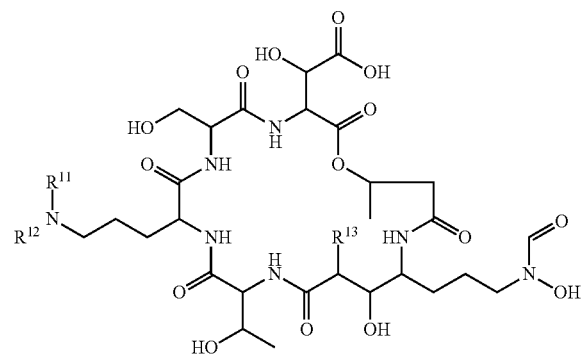

(II)

wherein
$R^{11}$ and $R^{12}$ are independently selected from H, OH and C=O;
$R^{13}$ is selected from H and $C_{1-4}$alkyl; or
a salt thereof.

In an embodiment, $R^{13}$ is H or $CH_3$.

In a further embodiment, the metallophore is a compound of the Formula III:

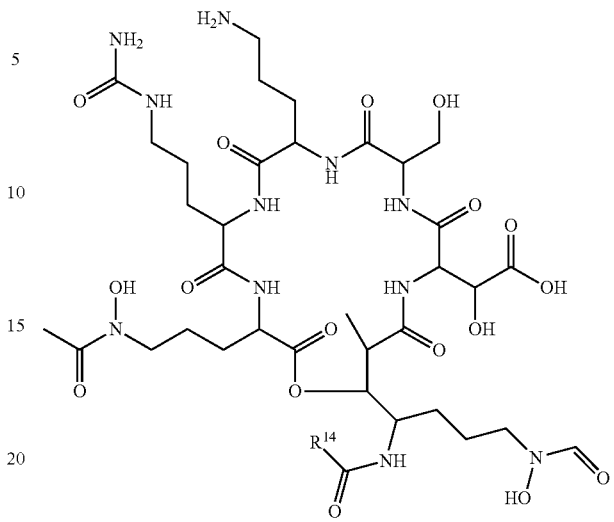

(III)

wherein:
$R^{14}$ is selected from $C_{1-20}$alkyl and $C_{1-20}$alkenyl; or
a salt thereof.

In an embodiment, $R^{14}$ is selected from $C_{8-16}$alkyl and $C_{8-16}$alkenyl. In a further embodiment, $R^{14}$ is selected from $C_9$alkyl, $C_{12}$alkyl, $C_{13}$alkyl, $C_{14}$alkyl and $C_{14}$alkenyl.

Figure 18:
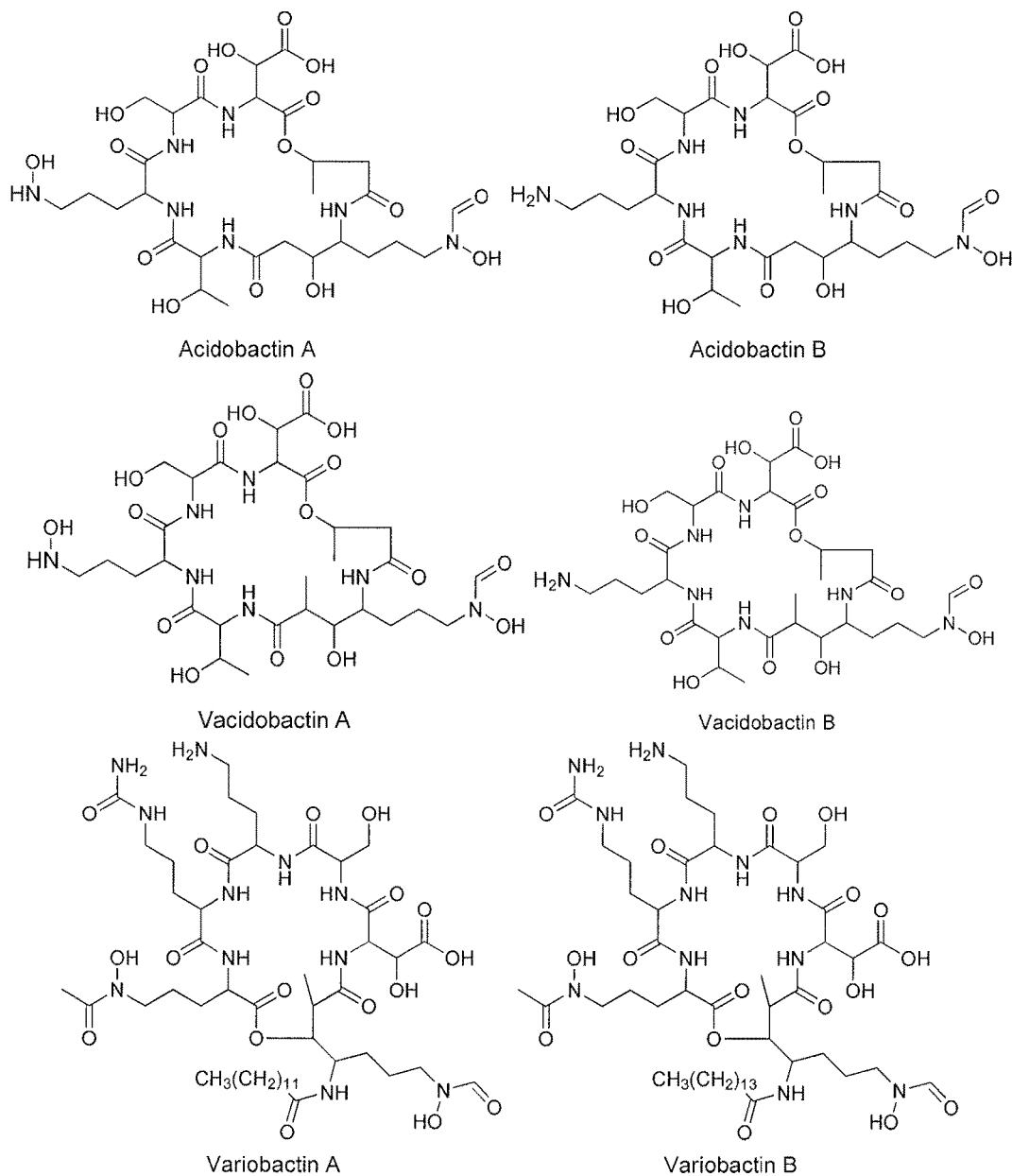
FIG. 18 shows chemical structures of metabolites related to delftibactin as follows: Acidobactin A; Acidobactin B; Vacidobactin A; Vacidobactin B; Variobactin A; Variobactin B; Variobactin C; Variobactin D; and Variobactin E, as further exemplary embodiments of the present application.
Figure 18:
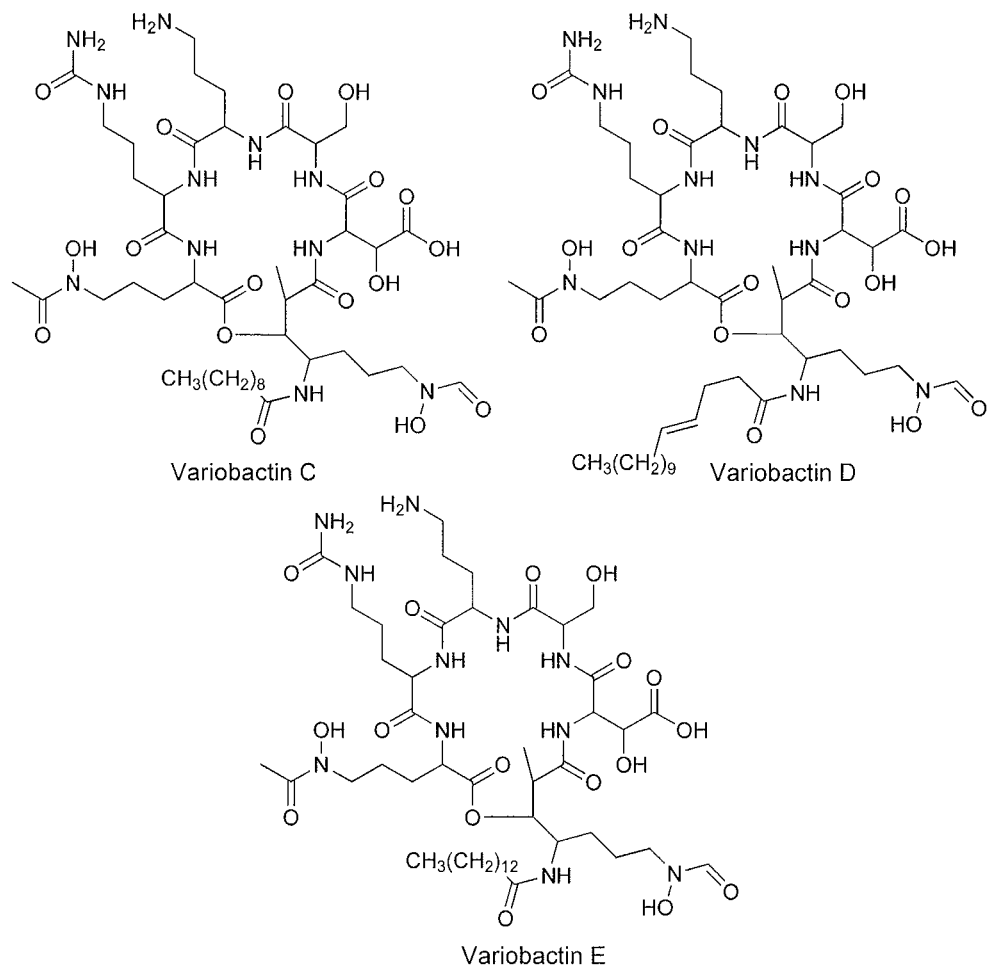

In a further embodiment, the metallophore is selected from delftibactin A and delftibactin B, and acidobactin A, acidobactin B, acididobactin C, acidobactin D, variobactin A, variobactin B, variobactin C, variobactin D and variobactin E as shown in FIG. 18, or a salt thereof.

The metallophores for use in the methods of the present application are prepared using methods known in the art of non-ribosomal peptide synthesis or they are isolated from a microorganism, again using methods known in the art. For example, the organism is cultured on a suitable medium and allowed to grow for a time sufficient for the metallophore metabolite to accumulate, for example about 1 to about 10 days, and the metallophore isolated from the medium using known techniques. The microorganism may be a naturally occurring microorganism or a genetically modified microorganism.

In an embodiment, conditions for contacting of the sample with the metallophore comprise mixing the sample and the metallophore at ambient (room temperature) for a time sufficient for the formation of solid gold, evidenced by the formation of a dark solid. In an embodiment, one or more, for example one, two or three, different metallophores are used in the methods of the application.

In a further embodiment, the conditions for contacting of the sample with the metallophore comprise first treating the sample to liberate the soluble gold ions so that the ions can interact with the metallophore. Examples of such pre-treatments are known in the art and include, for example, treatment with acid solutions (for e.g. aqua regia).

In an embodiment, the isolation of the solid gold or the gold nanoparticles is by any known means, for example, centrifugation or filtration.

The presence of solid gold in a sample can be observed using, for example, colormetric detection. The formation of a dark precipitate upon contact of the sample with the one or more metallophores of the present application indicates that the sample contained soluble gold.

In an embodiment, the soluble gold is a gold ion. In a further embodiment the soluble gold is $Au^{3+}$.

In a further embodiment, the observation of the sample for the presence of solid gold is performed in a quantitative manner as the amount of solid gold that is formed is proportional to the amount of soluble gold that was in the sample.

In an embodiment, the sample is a liquid solution. In a further embodiment, the sample is an environmental sample where the presence of toxic soluble gold is undesirable. In a further embodiment, the sample is an environmental sample where the presence of gold is desired. In an embodiment, the sample does not comprise substantial amounts of iron.

In another embodiment, the metallophores are also used to complex soluble iron and/or gallium in a sample.

In a further embodiment, the presence of soluble gold is observed using one of the detectors of the application (see section IV).

The present application also includes a use a metallophore to observe the presence of soluble gold in a sample, to remove soluble gold from a sample or to form solid gold or solid gold nanoparticles, wherein the metallophore is a microbial metabolite comprising a chelation core that binds to gold ions and wherein the microbial metabolite converts the soluble gold ions to solid gold ($Au^0$).

(III) Metallophores of the Application

The present application also includes novel compounds that act as metallophores and bind gold ions, converting the gold ions into solid gold. The novel compounds are isolated microbial metabolites.

Therefore, in further embodiment, the present application also includes an isolated compound of Formula I:

$R^9$ is

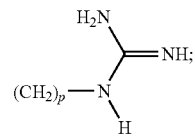

$R^{10}$ is selected from H and $C_{1-6}$alkyl; and
n, m and p are independently selected from 1, 2, 3 and 4, or a salt thereof.

In an embodiment, $R^1$ is selected from $CH_3$ and $CH_2CH_3$. In a further embodiment $R^1$ is $CH_3$.

In an embodiment, $R^2$ is selected from $CH_3$ and $CH_2CH_3$. In a further embodiment $R^2$ is $CH_3$.

In an embodiment, $R^3$ is $(CH_2)_nC(O)OH$ substituted with OH. In a further embodiment, n is 1.

In an embodiment, $R^4$ is selected from $C_{1-4}$alkyl substituted with OH. In another embodiment, $R^4$ is $CH(OH)CH_3$.

In an embodiment, $R^5$ is selected from H and $CH_3$. In another embodiment, $R^5$ is H.

In an embodiment $R^6$ is selected from $CH_2$, $CHCH_3$ and $CHCH_2CH_3$.

In an embodiment, $R^7$ is

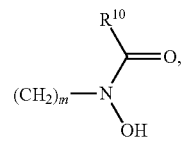

wherein m is 2 or 3 and $R^{10}$ is selected from H and $CH_3$. In a further embodiment, m is 3 and $R^{10}$ is H.

In an embodiment, $R^8$ is selected from $C_{1-2}$alkyl substituted with OH. In a further embodiment, $R^8$ $CH_2OH$.

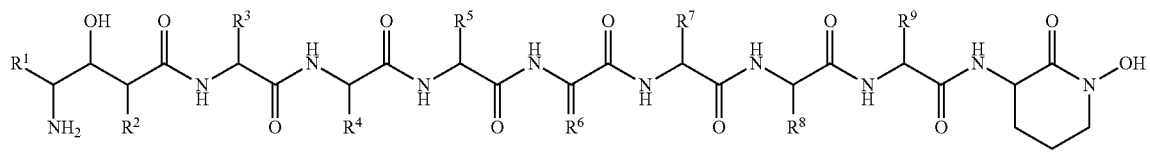

(I)

wherein
$R^1$ is selected from H and $C_{1-6}$alkyl;
$R^2$ is selected from H and $C_{1-6}$alkyl;
$R^3$ is $(CH_2)_nC(O)OH$, unsubstituted or substituted with OH;
$R^4$ is selected from $C_{1-6}$alkyl substituted with OH;
$R^5$ is selected from H and $C_{1-6}$alkyl;
$R^6$ is selected from $CH_2$, $C(C_{1-6}alkyl)(C_{1-6}alkyl)$ and $CHC_{1-6}alkyl$;
$R^7$ is

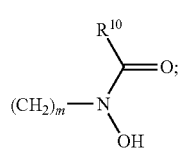

$R^8$ is selected from $C_{1-6}$alkyl substituted with OH;

In an embodiment $R^9$ is

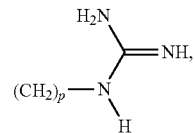

wherein p is 3 or 4. In an embodiment, p is 3.

In an embodiment the compound of Formula I is delftibactin A:

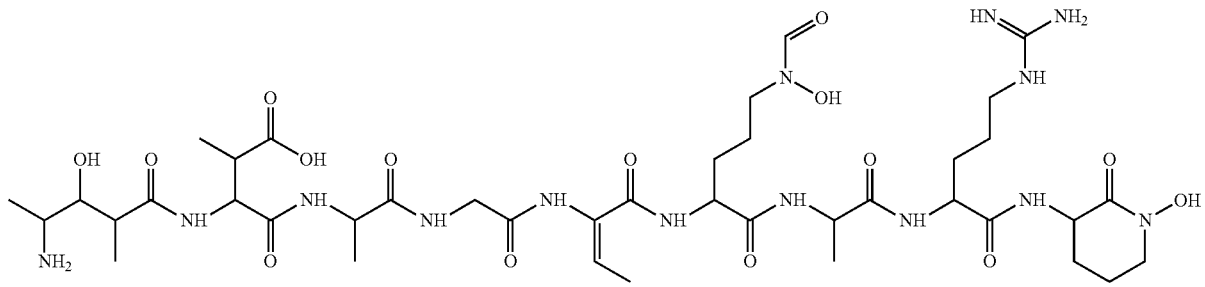 [SMILES: C/C=C(/NC(=O)CNC(=O)C(C)NC(=O)C(NC(=O)C(C)C(O)C(C)N)C(C)C(=O)O)C(=O)NC(CCCN(O)C=O)C(=O)NC(C)C(=O)NC(CCCNC(=N)N)C(=O)NC1CCCN(O)C1=O]

or delftibactin B:

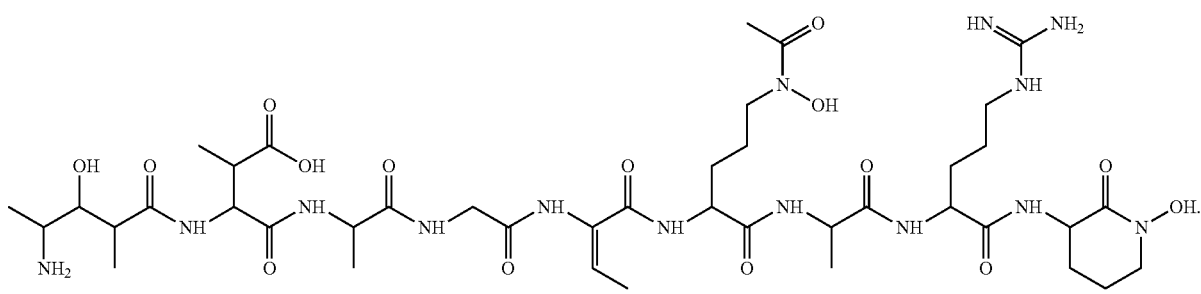 [SMILES: C/C=C(/NC(=O)CNC(=O)C(C)NC(=O)C(NC(=O)C(C)C(O)C(C)N)C(C)C(=O)O)C(=O)NC(CCCN(O)C(C)=O)C(=O)NC(C)C(=O)NC(CCCNC(=N)N)C(=O)NC1CCCN(O)C1=O]

In a further embodiment, the compound of Formula I is delftibactin A.

In yet another embodiment, the novel metallophore of the present application is an analog of delftibactin A which has gold chelating and solid gold forming ability. In a further embodiment, the analogs of delftibactin A are those comprising similar gene clusters to the genes that encode the enzymes (non-ribosomal peptide synthetases or NRPS)) for producing delftibactin A. For example, the genes that encode the enzymes for producing delftibactin A are used as the query in a BLAST search to identify similar gene clusters in other organisms.

In yet another embodiment, confirmation that a compound isolated from another organism is an analog of delftibactin A is made by comparing the mass spectral (MS) fragmentation pattern of the analog with that of delftibactin. If the analog possesses a similar MS fragmentation pattern to the MS fragmentation pattern of delftibactin then it is likely an analog of delftibactin. In an embodiment, the significance of a match in fragmentation patterns, indicating analogous structures is calculated using computational means, for example as described in Applicant's co-pending PCT Application Publication No. WO 2013/181758.

In a further embodiment, the present application also includes an isolated compound of Formula II:

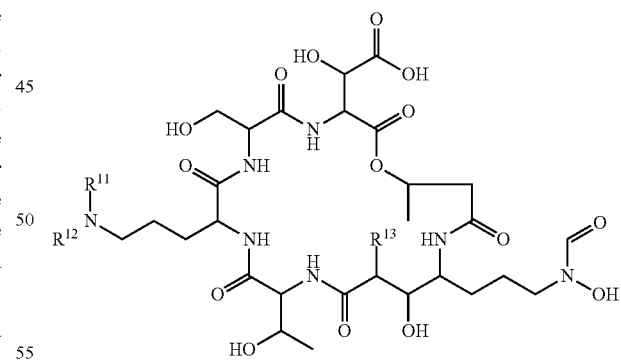

wherein $R^{11}$ and $R^{12}$ are independently selected from H, OH and C=O;

$R^{13}$ is selected from H and $C_{1-4}$alkyl; or a salt thereof.

In an embodiment, $R^{13}$ is H or $CH_3$.

In further embodiment, the present application also includes an isolated compound of Formula III:

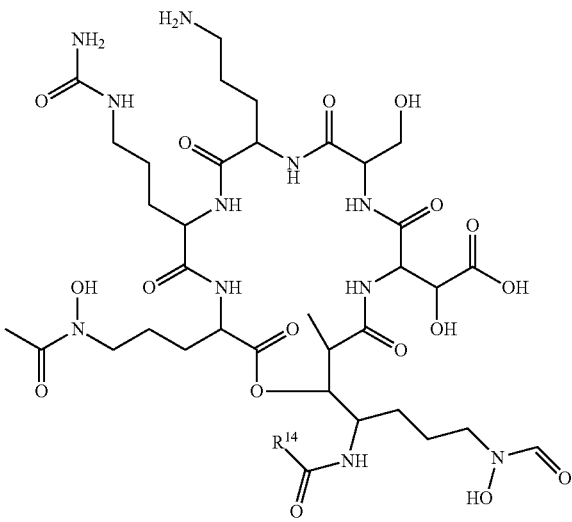
(III)

wherein:
$R^{14}$ is selected from $C_{1-20}$alkyl and $C_{1-20}$alkenyl; or a salt thereof.

In an embodiment, $R^{14}$ is selected from $C_{8-16}$alkyl and $C_{8-16}$alkenyl. In a further embodiment, $R^{14}$ is selected from $C_9$alkyl, $C_{12}$alkyl, $C_{13}$alkyl, $C_{14}$alkyl and $C_{14}$alkenyl.

In a further embodiment, the application includes an isolated compound selected from delftibactin A and delftibactin B, and acidobactin A, acidobactin B, acididobactin C, acidobactin D, variobactin A, variobactin B, variobactin C, variobactin D and variobactin E as shown in FIG. 18, or a salt thereof.

The compounds of the present application may be prepared using methods known in the art of non-ribosomal peptide synthesis or they may be isolated from a microorganism, again using methods known in the art. For example, the organism is cultured on a suitable medium and allowed to grow for a time sufficient for the desired compound to accumulate, for example about 1 to about 10 days, and the desired compound isolated from the medium using known methods. The microorganism may be a naturally occurring microorganism or a genetically modified microorganism.

(IV) Detectors of the Application

There is a need for an inexpensive, fast and easy method to test soil samples for gold within land claims. Current practices involve the collection of several thousand soil samples per square kilometer across a claim after which each sample is packaged a shipped to a remote facility for metal analysis. Subsequent analysis involves a variety of experimental procedures and can range in price from $25-50, taking up to several weeks for results. Other methods involving infield analysis tools, such as X-Ray fluorescence (XRF) analyzers, are expensive and require extensive sample preparation for accurate results. Developing an inexpensive, infield colorimetric test strip indicator that can quickly assay the concentration of gold within a soil sample will not only reduce assay costs and shipping related expenses, but will also decrease the time a prospector must wait to determine the location of gold deposits within his claim.

Areas of use for colorimetric test strips include industrial and environmental surveying, analysis, and quality control. There continues to be a need for a colorimetric test strip of enhanced sensitivity for determination of gold. It is desirable that a test strip have the necessary detection capability. Stability of the indicator, uniform color development and stability of the developed color would be advantageous. Moreover, a broad range of sensitivity would be beneficial. It would be also advantageous for the test strip to be economical to manufacture.

Colorimetric detectors useful for and method for the analysis of gold are included in the present application. The detector includes a carrier and a metallophore of the present application as a colorimetric indicator.

Accordingly, the present application also includes a detector for gold comprising a carrier and one or more metallophores, wherein the one or more metallophores are microbial metabolites comprising a chelation core that binds to gold ions and wherein the microbial metabolites convert the soluble gold ions to solid gold ($Au^0$). In an embodiment, the one or more metallophores are one or more of the compounds of the Formula I, II or III, or a salt thereof.

In an embodiment, the carrier is any solid support matrix including $C_{18}$-bonded silica, silica, alumina and other stationary phase materials. In embodiment, the one or more of the compounds of Formula I, II and/or III are covalently linked to a solid support matrix, physically entrapped within a matrix (for example a sol gel matrix) or are held on or within a matrix using any known mechanism. In further embodiments, the one or more of the compounds of Formula I, II and/or III are distributed on or in the matrix as a single concentration or as a gradient of concentrations to facilitate quantification of gold ions where applicable.

In an embodiment, during an analysis, the carrier is contacted with a liquid to be analyzed, and the liquid caused to flow through the carrier and to contact the one or more of the compounds of Formula I, II and/or III over a selected period of time. When the carrier is dipped into the liquid, a gentle swirling action is beneficially used to cause the liquid to be in flowing contact with the compound(s). After the selected contact time, the carrier is evaluated for detectable color change advantageously by viewing the area of the carrier defined by the contact zone (aperature).

In an embodiment, the color change is compared to a standardized color chart to determine the gold concentration. The color change intensity that develops, increases as the concentration of the gold in the sample increases and, in an embodiment, is quantitatively determined with reproducible sensitivity and accuracy.

In further embodiments, the present application includes several ways by which the one or more of the compounds of Formula I, II and/or III are used as a detector of gold. In a first embodiment, the detector is based on a thin layer chromatography concept, for example as shown in FIG. 20A. In this embodiment, a concentration gradient of one or more of the compounds of Formula I, II and/or III is absorbed onto a test strip and is used to determine the concentration of gold in a solution after fixed incubation period. This occurs whereby solutions with low concentrations of gold will be captured lower on the strip by the compound(s) as the liquid moves upwards and solutions with high concentrations of gold ions will saturate the compound(s) lower on the strip and move higher creating a higher band of compound-induced blackening. In a second embodiment, a test strip comprising one or more of the compounds of Formula I, II and/or III absorbed thereto is submerged in liquid sample to determine gold concentration, for example as shown in FIG. 20B. Varying the ratio of the compound(s) to gold causes differential darkening, allowing for easy quantification and detection of gold from a solution. In a third embodiment, one or more of the compounds of Formula I, II and/or III are absorbed within a chromatographic column to provide a similar colorimetric indication as the submerged test strip. This embodiment advantageously allows for increased sample volumes to be used, which can increase the signal (blackening) or decrease the limit of detection within a sample (see for example, FIG. 20C).

The above disclosure generally describes the present application. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1: Isolation, Characterization and Reactions of Delftibactin A and B Methods
General Experimental Procedures 1D ($^1$H and $^{13}$C) and 2D ($^1$H-$^{13}$C and $^1$H-$^{15}$N HMBC, HSQC, NOESY, and COSY) NMR spectra were recorded on a Bruker AVIII 700 MHz NMR spectrometer in $D_2O$ ($D_2O$; Cambridge Isotope Laboratories). High resolution MS spectra were collected on a Thermo LTQ OrbiTrap XL mass spectrometer (ThermoFisher Scientific, USA) with an electrospray ionization source (ESI) and using CID with helium for fragmentation. LCMS data was collected using a Bruker AmazonX ion trap mass spectrometer coupled with a Dionex UltiMate 3000 HPLC system, using a Luna $C_{18}$ column (250 mm×4.6 mm, Phenomenex) for analytical separations, running acetonitrile and dd$H_2O$ as the mobile phase.

Bacterial Strains

Delftia acidovorans was ordered from the German Resource Centre for Biological Material (DSMZ, DSM No. 39). Delftia acidovorans was cultured on Acidovorax Complex Media (Pinel et al., 2008) (ACM) plates at 30° C. The ΔdelG strain was initially grown in the presence of 30 μg/mL tetracycline. Environmentally isolated D. acidovorans strains D27L and D126L were found in soil samples collected around McMaster University from June to August 2010. Environmental isolates were identified as D. acidovorans strains based on 16S sequence alignment, using 16S sequences that were amplified from single colonies using the universal 16S primers (Weisburg et al., 1991): 27f (AGAGTTTGATCMTGGCTCAG [SEQ ID NO:1]) and 1525r (AAGGAGGTGATCCAGCC [SEQ ID NO:2]).

Gold Precipitation on Agar Plates

Wildtype and ΔdelG Delftia acidovorans was streaked onto a Chelex treated (deferrated) Acidovorax Complex Media (ACM) agar plate and grown for 3 days at 30° C. The plate was then overlaid with 10 mL of 0.5% agar containing 10 mM $AuCl_3$. Gold complexing comparison to other bacteria was carried out as follows. Ten microliters of an overnight culture of D. acidovorans, D. acidovorans ΔdelG, or C. metallidurans were placed onto deferrated ACM plates and grown for 3 days at 30° C. The plates were overlaid with $AuCl_3$ as described above. Both images were taken after 2 h of incubation at room temperature.

D. acidovorans 96-Well Plate Gold Bioassay

After brief centrifugation to remove particulates, 100 μL of the D. acidovorans HP20 extract was loaded onto a Waters Alliance 2695 separations module HPLC equipped with a photodiode array and fractionated into a 96-deep well plate, collecting 96 fractions starting at 2 min and finishing at 56 min, fractions were obtained approximately every 30 s. The mobile phase was curved (curve 8) from 5% acetonitrile, 95% water at 2 minutes to 80% acetonitrile at 45 min at a flow rate of 3 mL/min. Plates were dried overnight in a GeneVac HT4 series 2, resuspended in 60 μL of dd$H_2O$, and 25 μL were placed in fresh plates along with 25 μL 10 mM $AuCl_3$ and left to react at room temperature for 30 min.

Identification of Delftibactin a Biosynthetic Gene Cluster and Adenylation Domain Specificity Delftibactin A NRPS and PKS genes were identified using the BLAST function of IMG (http://img.jgi.doe.gov), using the sequence of pksJ as a query. Adenylation domain specificities were assessed using NRPS Predictor (Rausch et al., 2005) or NRPS-PKS (Ansari et al., 2004), and the 10 residue codes (Stachelhaus et al., 1999) of each entry and its top scoring hit were recorded. For the alignment of the adenylation domains specific for hydroxylated ornithine, the delftibactin A adenylation code and the vicibactin adenylation code were determined with NRPS Predictor (Rausch et al., 2005) and aligned manually as neither database contained domains with homologous sequences.

Construction of the ΔdelG D. acidovorans Strain

All primers and plasmids used in this process are described in Table 2. If not stated explicitly, genetic manipulations and molecular biology techniques followed those from Cold Spring Harbor Protocols, available on the internet.

A knockout plasmid for D. acidovorans was constructed by inserting a 2 kb PCR product of delG (primers 2kbNRPS2Xba2 and 2kbNRPS2Sac2) into pUC19 using Xba1 and Sac1 digest sites, ligating with T4 ligase, transforming into chemically competent DH5α (Invitrogen), and plating on LB with 100 μg/mL ampicillin. Positive clones were identified by colony PCR with 2kbNRPS2Xba2 and 2kbNRPS2Sac2, and verified through digestion following an overnight growth and plasmid miniprep using a QIAprep Spin Miniprep Kit (Qiagen). A clone containing a 2 kb insert was digested with Not1 to cut in the middle of the 2 kb insert, treated with calf intestinal phosphatase (CIP), and gel extracted to remove remaining CIP. A tetracycline resistance cassette was amplified from pLLX13 (primers TetNotF and TetNotR), purified, digested with Not1, and ligated with the digested vector. This ligation was transformed into chemically competent DH5α (Invitrogen) and plated on LB with 100 μg/mL ampicillin and 10 μg/mL tetracycline. Positive colonies were confirmed by PCR with TetNotF and TetNotR, and verified with digestion with Xba1 and Sac1, or with Not1, following an overnight growth and plasmid miniprep. The resulting plasmid was modified further by digesting with HindIII, treating with CIP, and gel extracting to remove remaining CIP. An oriT was amplified from pLLX13 with primers OriTF and OriTR, purified, digested with HindIII, and ligated with the cut vector before transforming into chemically competent DH5α and plating on LB with 100 μg/mL ampicillin and 10 μg/mL tetracycline. Positive colonies were identified with PCR using OriTF and OriTR, and verified by digestion following an overnight growth and plasmid miniprep. The final plasmid (pDEL19) was transformed into chemically competent *E. coli* ET12567 carrying the helper plasmid pUZ8002, plating on LB with 10 μg/mL tetracycline, 30 μg/mL chloramphenicol, and 25 μg/mL kanamycin. Positive transformants were grown in 3 mL LB with antibiotics overnight at 37° C., alongside a 3 mL ACM growth of *D. acidovorans* at 30° C. 1 mL of the donor *E. coli* and 1 mL of the recipient *D. acidovorans* were centrifuged separately and washed twice with fresh LB. Cells were resuspended in 1 mL LB and mixed 1:1, dispensing 300 μL on nutrient agar plates and leaving to grow overnight at 30° C. Cells were scraped and resuspended in 3 mL LB, plating 50 μL on LB plates containing 30 μg/mL tetracycline and 100 μg/mL apramycin to remove *E. coli*. Colonies were observed and tested for growth in LB with antibiotics at 30° C. and 200 rpm, with viable cultures streaked on LB plates with 30 μg/mL tetracycline. Colony PCR with TetNotF and TetNotR was used to confirm the presence of the tetracycline cassette. Chromosomal integration of the tetracycline cassette was confirmed by PCR with TetNotR and NRPS2Seq2 primers.

16S Alignment and Delftibactin A Production in Environmental Strains

Environmental isolates from around the McMaster University campus were identified as *D. acidovorans* strains based on 16S sequence alignment, using 16S sequences that were PCR amplified from single colonies (see above). Using these sequences and the 16S sequence for the *D. acidovorans* genome strain SPH1 from GenBank, along with the sequence for a gold biofilm isolate of *D. acidovorans* (Accession no. GU013680) (Reith et al., 2010) were aligned with Geneious software version 4.8.5 (Drummond et al., 2009), using a Tamura-Nei genetic distance model, a Neighbor-Joining tree building method featuring a global alignment with free end gaps. Isolated strains were grown for 3 days at 30° C. and 190 rpm in 1 L of ACM which had been treated with Chelex100 resin to limit the iron concentration. Cultures were centrifuged at 7000 rpm to remove the cell mass, and supernatants were treated with 20 g/L washed HP20 resin (Dialon). After 1 h of shaking with the supernatant, HP20 was collected by Buchner funnel vacuum filtration and eluted with 400 mL of methanol. This was evaporated to dryness, resuspended in 50% methanol and water, and injected into a Waters AutoPure LCMS using a similar method as above. MassLynx software was used to generate the 1033 m/z extracted ion chromatograms for each extract. Fragmentation of these compounds was carried out on a Bruker AmazonX ion trap mass spectrometer.

Delftibactin:Au(III) Precipitation Measurements

The gold-delftibactin A interaction was determined through two separate experiments. First, $AuCl_3$ was held constant at 2.5 mM and the interaction with delftibactin A was monitored by measuring the absorption of $AuCl_3$ remaining in solution after precipitation by delftibactin A through comparison with a standard curve. Briefly, 2.5 mM $AuCl_3$ was incubated with 5, 2.5, 1.25, 0.6125, 0.3063, and 0.1531 mM delftibactin A for 1 h. Solutions were filtered with a 0.22 μM Acrodisc (Pall, USA) to remove insoluble delftibactin A-gold precipitate. 100 μl of the filtered reaction was placed in a 96-well plate and the absorbance was read at 300 nm using a SpectraMax 384 Plus (Molecular Devices, USA). Absorption was compared to an $AuCl_3$ standard curve to determine the concentration of $AuCl_3$ remaining in solution. To monitor the amount of delftibactin A remaining in solution after reaction with gold a similar experiment was conducted. Delftibactin A (2.5 mM) was incubated with 5, 2.5, 1.25, 0.6125, 0.3063, and 0.1531 mM $AuCl_3$ for 1 h.

Solutions were filtered similar to above. Reaction mixtures were analyzed using a Waters Alliance 2695 RP-HPLC separations module, equipped with a Waters 2998 photo-diode array and a Luna 5u $C_{18}$ column (250×4.60 mm, Phenomenex). The mobile phase was linear from 2% acetonitrile, 98% water+5 mM $(NH_4)_2CO_3$ at 2 min to 14% acetonitrile at 18 min at a flow rate of 1 mL/min. The UV peak associated with delftibactin A ($T_r$=12.29 min) was integrated and compared to a standard curve.

Transmission Electron Microscopy of Delftibactin A:Au(III) Complexes

Delftibactin A was reacted with $AuCl_3$ with a molar ratio equal to 2:1 for ten minutes. Each separate reaction of delftibactin A with $AuCl_3$ was examined using a Phillips CM-10 transmission electron microscopy operating at 80 kV. The whole-mount sample was absorbed and dried on a formvar-carbon coated 100-square mesh copper grid and rinsed with filter sterilized, de-ionized water to remove any salt precipitates.

Ga-Delftibactin A—Gold Interaction

Gallium bound delftibactin A was adjusted to 10 mM and mixed 1:1 with an equimolar solution of $AuCl_3$, alongside purified delftibactin A and water control. The reaction mixture was monitored at room temperature for 30 min.

Gold Detoxification by Delftibactin A

The assay was set up as follows: 50 μL of $ddH_2O$ containing 3.2, 1.6, 1.4, 1.2, 1.0, 0.8, 0.6, 0.4, and 0.2 mM delftibactin A was added in quadruplicate to wells within a 96-well plate. A 1.6 mM stock solution of $AuCl_3$ was made and 50 μL was added to each well containing delftibactin A. No-delftibactin A and no-$AuCl_3$ controls containing only water were also added to the 96-well plate in quadruplicate. This was incubated for 30 min at room temperature, during which time 10 mL of an overnight culture of *D. acidovorans*, grown in ACM was centrifuged and resuspended in 5 mL sterilized $ddH_2O$. After 30 min incubation of $AuCl_3$ with delftibactin, 100 μL of concentrated culture was added to each well. Final concentration of $AuCl_3$ was 400 μM and the final concentrations of delftibactin A were 800, 400, 350, 300, 250, 200, 150, 100, and 50 μM. After 30 minutes of incubation at room temperature, mixtures were serial diluted and plated onto Nutrient Agar plates and incubated at 30° C. Colonies were counted after 24 h of growth. Results are shown as mean±s.d.; n=4. To assess whether *D. acidovorans* could grow in the presence of the gold precipitate, several milligrams of delftibactin A and $AuCl_3$ were reacted 1:1 overnight and centrifuged, and washed once with water to concentrate the precipitate. The precipitate was resuspended in $ddH_2O$ at a final concentration of 100 mM, calculated using a molecular weight of 1227 g/mol, corresponding to a gold-delftibactin A species. *D. acidovorans* was grown overnight in a 96-well plate in 100 μL of ACM containing 20 μM to 10 mM gold precipitate or $AuCl_3$. No growth was observed in any well containing $AuCl_3$, while full growth was observed in every well containing the corresponding amount of precipitate. The MIC of $AuCl_3$ was determined to be roughly 10 μM.

Gold Detoxification in Chronic Exposure by Delftibactin A in Presence and Absence of Iron Twenty microliter reactions were set up as follows: i) water only, ii) 5 mM delftibactin A, iii) 5 mM $AuCl_3$ iv) 5 mM $FeCl_3$ v) 5 mM $AuCl_3$+5 mM $FeCl_3$ vi) 5 mM delftibactin B+5 mM $AuCl_3$ vii) delftibactin B+5 mM $AuCl_3$+5 mM $FeCl_3$ viii) delftibactin B+5 mM $FeCl_3$. Reactions were initiated by the addition of delftibactin and images were taken at time points indicated. After 2 h, reactions were serially diluted to 30 μM final concentration in ACM containing *D. acidovorans* ΔdelG diluted 1:1000 from an overnight culture. Optical density was monitored using a TECAN Sunrise™ microplate reader at 600 nm for 36 h. Results are a mean of three growth curves for each condition from a single representative experiment. As a second test of delftibactin protective capacity, *D. acidovorans* ΔdelG cells from an overnight culture were inoculated 1:1000 into 100 µL ACM in a 96-well plate containing 0 or 10 µM AuCl$_3$, and then provided 0 or 100 µM delftibactin. Cultures were grown for 84 h at 250 rpm at 30° C. in a TECAN Sunrise™ microplate reader, measuring at 600 nm to assess growth. Results are a mean of three growth curves for each condition from a single representative experiment.

Gold Protective Comparison of Delftibactin A and B.

Twenty microliter reactions were set up as follows: water only, 5 mM AuCl$_3$, 5 mM AuCl$_3$+delftibactin A, and 5 mM AuCl$_3$+delftibactin B. Reactions were initiated with the addition of delftibactin A or B. After 2 h, reactions were serially diluted to 125 µM in ACM containing *D. acidovorans* ΔdelG diluted 1:1000 from an overnight culture. Optical density was monitored using a TECAN Sunrise™ microplate reader at 600 nm for 36 h. Results are a mean of three growth curves for each condition from a single representative experiment.

Delftibactin-Mediated Protection Against Gold Toxicity

Cultures of *D. acidovorans* wild type and *D. acidovorans* ΔdelG were grown in deferrated ACM for 2 days at 30° C. In 96-well plates, 200 µL of wild type or mutant grown culture were incubated in the presence and absence of 100 µM AuCl$_3$. At the same time, the mutant culture was also complemented with 30 sM delftibactin (biological levels) in the presence of 100 µM AuCl$_3$. After 30 minutes, cultures were serially diluted in water and plated on LB agar to determine the colony forming units of *D. acidovorans* after gold exposure. Results are shown as mean s.d.; n=4; Two-tailed student's t-test.

Measuring Delftibactin A Production Following Depletion by Gold

Cultures of *D. acidovorans* were grown in 10 mL ACM in 50 mL Falcon tubes for 48 h, at which point both growth and delftibactin A production had ceased. Cultures were then pelleted by centrifugation at 4500 rpm for 30 min at 4° C. Supernatants were kept separate and moved into labeled, sterile 50 mL Falcon tubes while cell pellets were kept on ice. Initial delftibactin A concentrations were assessed by filter sterilizing 400 µL of each supernatant and placing it in a HPLC sample vial, storing at 4° C. Supernatants were then adjusted to 0, 10, or 30 µM AuCl$_3$ with the appropriate volume of 10 mM AuCl$_3$ and left to react at room temperature. After 12 h supernatants were returned the appropriate cell pellets and resuspended by vortexing before taking a second 400 µL sample to assess delftibactin A depletion by gold treatment. Cultures were returned to the incubator and left shaking for another 48 h before a final sample was taken. Delftibactin A concentrations were assessed by MRM-LCMS for delftibactin A, with washes between each sample. Values of integrated delftibactin A peaks were normalized to the untreated control and represent the percent increase in delftibactin A concentration (± propagated error) observed 48 h following gold precipitation; n=6.

MRM-LCMS Measurement of Delftibactin A Production in Response to Iron

Cultures of *D. acidovorans* were grown for 48 h in 10 mL cultures of deferrated ACM resupplied with FeCl$_3$ in varying concentrations. Iron concentrations and corresponding delftibactin A concentrations in the filter sterilized supernatants are listed below in Table 3. Delftibactin A concentrations were established using MRM-LCMS. Results are shown as mean±s.d.; n=3.

Citrate-Gold and Delftibactin A-Gold Comparison

Stock 10 mM solutions of sodium citrate and purified delftibactin A were mixed with and equimolar solution of AuCl$_3$ and allowed to react at room temperature in 1.5 mL Eppendorf tubes. Photographs were taken from the initial addition of gold to 1 h exposure. Similarly, TEM experiments were performed by mixing 10 mM stock solutions of AuCl$_3$ and either delftibactin A or sodium citrate 1:1 on a formvar-carbon coated 100-square mesh copper grid, imaging after 10 min AuCl$_3$ exposure.

Discussion

Figure 2:
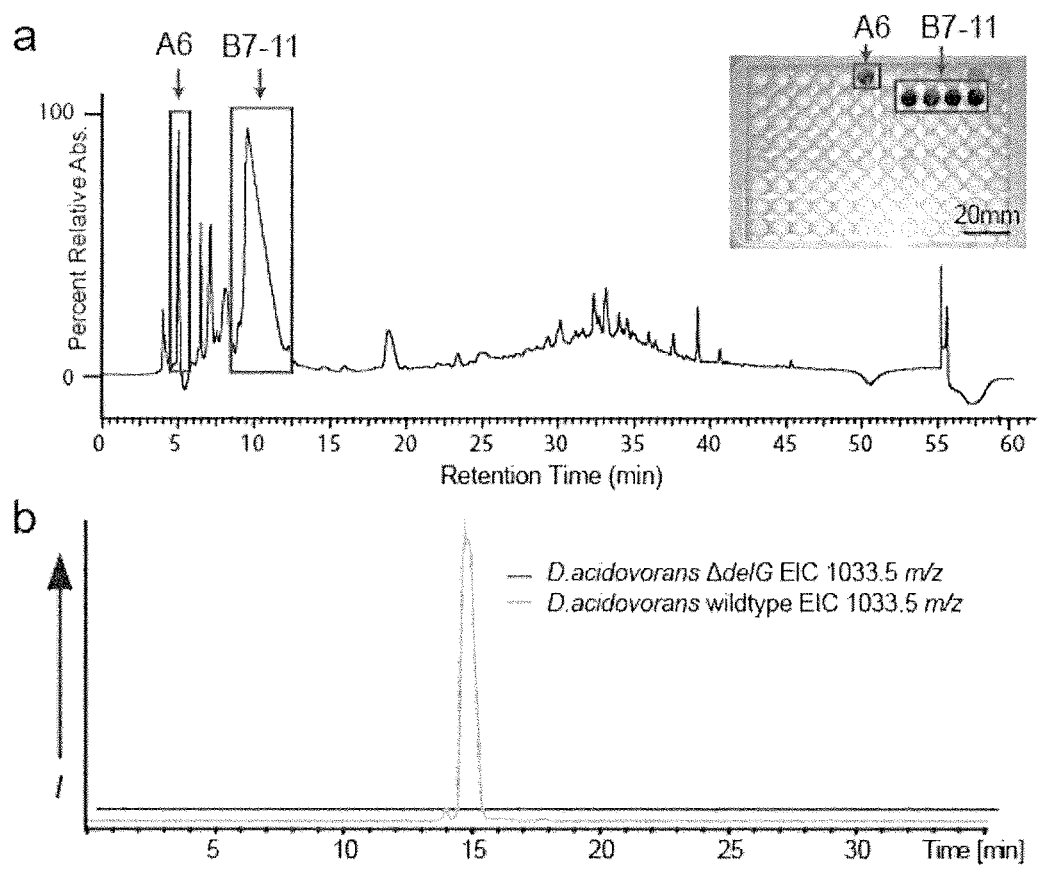
FIG. 2 (a) shows the HPLC chromatogram of metabolites extracted from D. acidovorans cultures. Various fractions were separated by HPLC into a 96-well plate, and reacted with 5 mM $AuCl_3$. The inset shows blackening in the wells for fractions A6 and B7-11 which indicates gold nanoparticle formation. These active wells were found to contain a common peptidic metabolite; (b) extracts of wildtype and ΔdelG D. acidovorans analyzed by LCMS. The extracted ion chromatogram of the wildtype specific compound associated with gold precipitation is shown.
Figure 3:
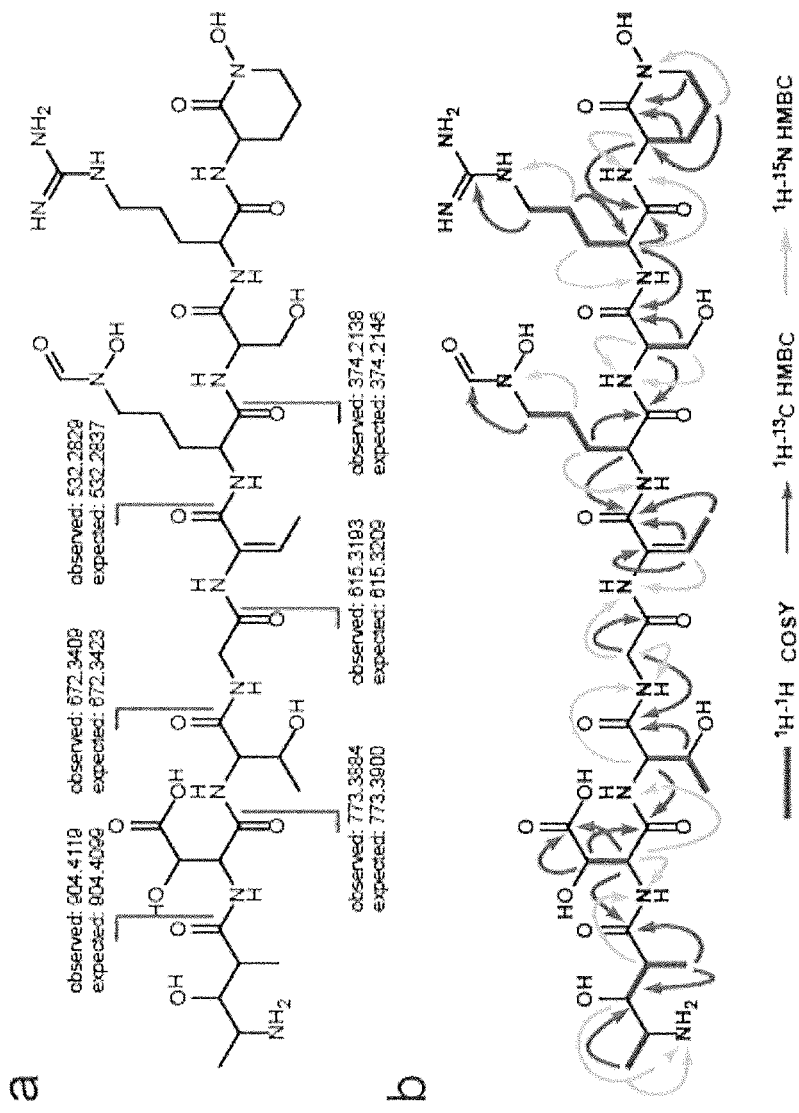
FIG. 3 shows (a) the high resolution mass fragmentation and (b) 2D NMR spin systems for $^1H$-$^{13}C$ heteronuclear multiple bond correlation (HMBC), $^1H$-$^1H$ correlation spectroscopy (COSY) and $^1H$-$^{15}N$ HMBC for delftibactin A in $D_2O$.

An assay was developed to define whether the mechanism of biomineralization used by *D. acidovorans* was an extracellular or an intracellular one, to reveal mechanisms of how *D. acidovorans* protects itself from toxic soluble Au$^{3+}$ and how it may relate to gold deposition. It was reasoned that if a cell-associated mechanism was predominant or exclusive, the bacteria would accumulate insoluble gold particles (Kashefi et al., 2001) whereas, if an extracellular gold reduction occurs at the cell surface or within the area surrounding microbial colonies, blackening would result due to gold reduction and the creation of solid gold particles. *D. acidovorans* and *C. metallidurans* were grown on agar plates and then flooded with solutions of Au(III)—the dominant form of soluble gold found in terrestrial conditions (Reith et al., 2009; Usher et al., 2009). Following gold exposure darkened zones developed surrounding colonies of *D. acidovorans* but not *C. metallidurans*. These blackened zones suggested that *D. acidovorans* generated a diffusible metabolite that acts to generate reduced solid gold forms. The *D. acidovorans* genome was investigated for genes that may be associated with a unique small molecule biosynthesis pathway that is absent from *C. metallidurans*. For example, polyketides and non-ribosomal peptides (NRP) are classes of secondary metabolites that bacteria use to promote environmental fitness (Vining, 1990) but are not required for growth, and include members that function to bind metals (e.g. Fe, Cu) (Hider et al., 2010; Kim et al., 2004; Chaturvedi et al., 2012). Indeed, the analysis identified a candidate non-ribosomal peptide synthetase/polyketide synthase (NRPS/PKS) gene cluster (Daci_4753-4759) for an unknown secondary metabolite that, according to bioinformatic analysis (Stachelhaus et al., 1999) and in silico predictions, was expected to be a polar peptidic small molecule (FIG. 1). Upstream, flanking these biosynthetic genes is a tripartite heavy metal efflux pump (Diels et al., 1995; Salem et al., 2012) (Daci_4763-4765; 68% identical and 83% similar to the CzcA-like HmyA heavy metal efflux pump from *C. metallidurans* CH34 [Rmet_4123]) perhaps supporting a role of this cluster being associated with gold detoxification. Downstream genes were associated with metallophores that bind iron (siderophores), and specifically, genes for their reception and regulation (Hider et al., 2010). To reveal whether the Daci_4753-4759 (del) cluster (FIG. 1) was associated with the observed gold precipitation, an insertional inactivation of the non-ribosomal peptide synthetase gene (Daci_4754) was constructed, and the resulting mutant strain was compared to the wild-type in the soluble gold exposure agar plate assay. Unlike the wild-type, colonies of the ΔdelG strain were deficient in producing a blackening zone. To further reveal whether end products from this biosynthetic locus were solely responsible for the gold precipitation, broth extracts of the entire *D. acidovorans* secreted metabolome were generated and the mixtures were subjected to chromatographic separations with LC-MS, and the separated contents were eluted into a 96-well plate. Within the water soluble fractions a select number of wells (A6, B7-11) recapitulated the gold activity (FIG. 2a). Well fractions capable of gold precipitation were analyzed further and were found to share a peptidic compound that closely matched the molecular weight of the predicted del non-ribosomal peptide, which was absent in extracts from the ΔdelG strain (FIG. 2b) that lack gold-precipitating metabolites. This peptidic compound could be identified in supernatants in concentrations in excess of 200 μM (Table 3), enabling its isolation and structure determination by high resolution mass spectrometry (FIG. 3a) and NMR spectroscopy (FIG. 3b), revealing a novel linear polyketide-non-ribosomal peptide consistent with the structural prediction, which was named delftibactin A (FIG. 4). *D. acidovorans* environmental isolates were also screened for their ability to produce delftibactin A, resulting in its identification in all tested isolates.

Figure 5:
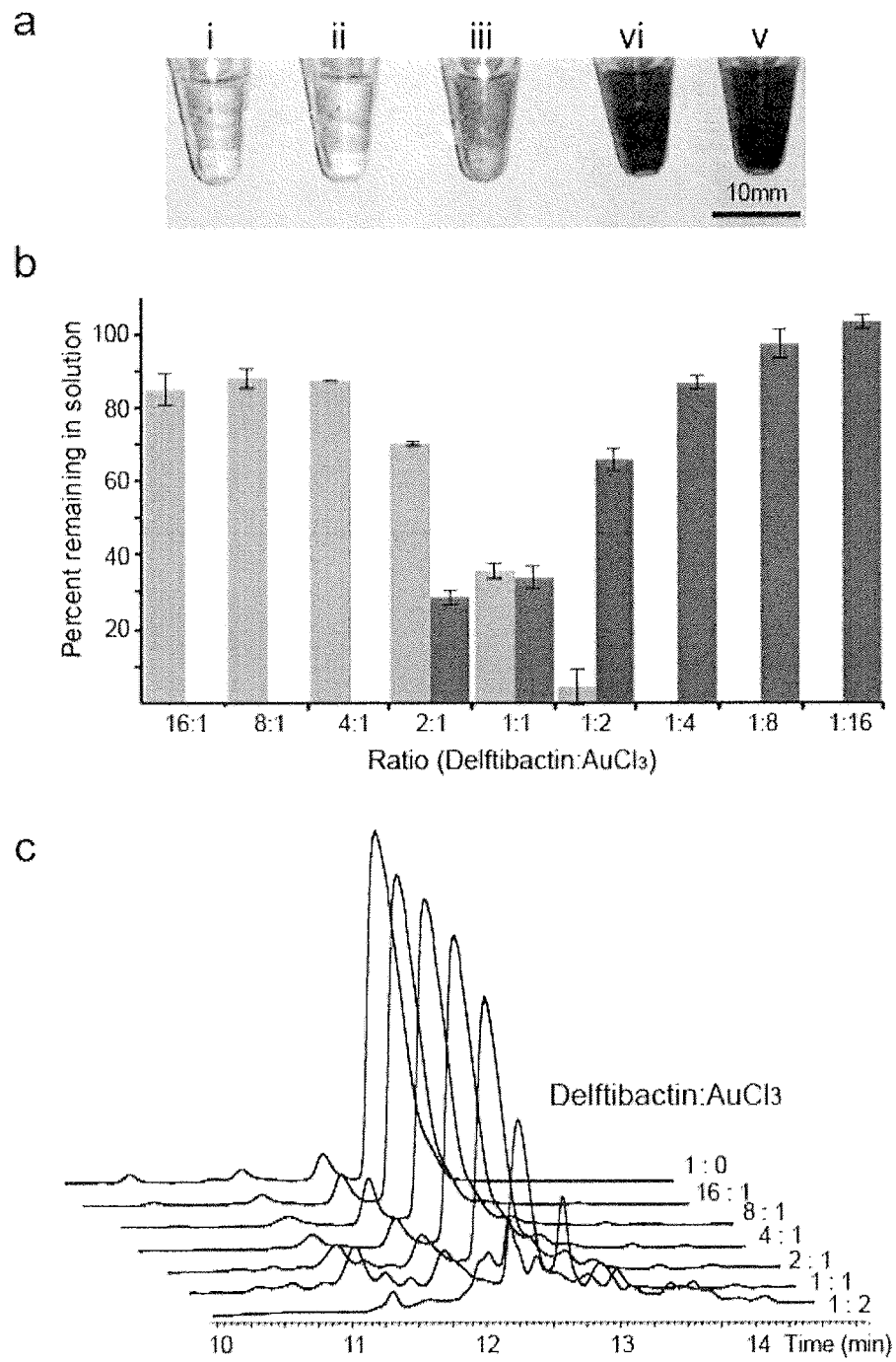
FIG. 5 shows (a) pictures of increasing concentrations of delftibactin A in the presence of 2.5 mM $AuCl_3$ causing an increase in gold nanoparticle formation. Images were taken 30 min after the addition of delftibactin A in the following concentrations: i) 0.3125 mM ii) 0.625 mM iii) 1.25 mM iv) 2.5 mM and 5 mM; (b) a bar graph of the amount of delftibactin A and gold remaining in delftibactin A-$AuCl_3$ reaction supernatants. Solutions of 2.5 mM $AuCl_3$ were reacted with 1:8, 1:4, 1:2, 1:1, and 2:1 equivalents of delftibactin A for 30 minutes. Delftibactin A remaining in solution was determined by integration at 220 nm (lighter bars) by HPLC. The amount of gold remaining in solution was measured at 300 nm (darker bars) by UV absorbance spectrometry. Results are shown as mean±s.d; n=3; and (c) delftibactin A depletion in representative HPLC chromatograms of delftibactin A-$AuCl_3$ supernatants.
Figure 6:
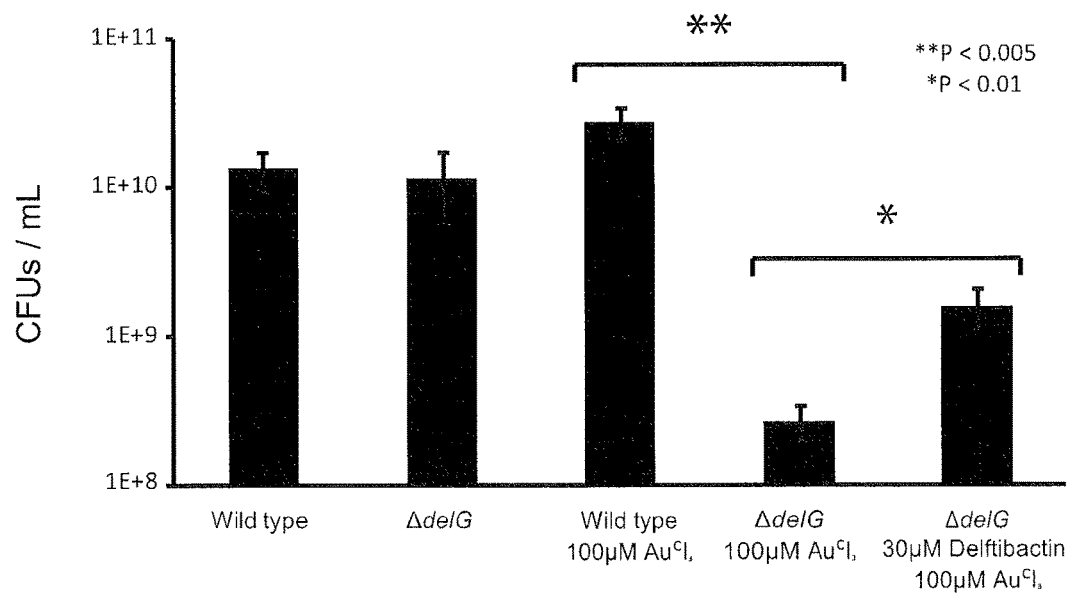
FIG. 6 is a bar graph showing that delftibactin A-null *D. acidovorans* has increased sensitivity to gold toxicity that can be rescued by the addition of delftibactin A. Results are shown as mean±s.d.; n=4; Two-tailed student's t-test.
Figure 7:
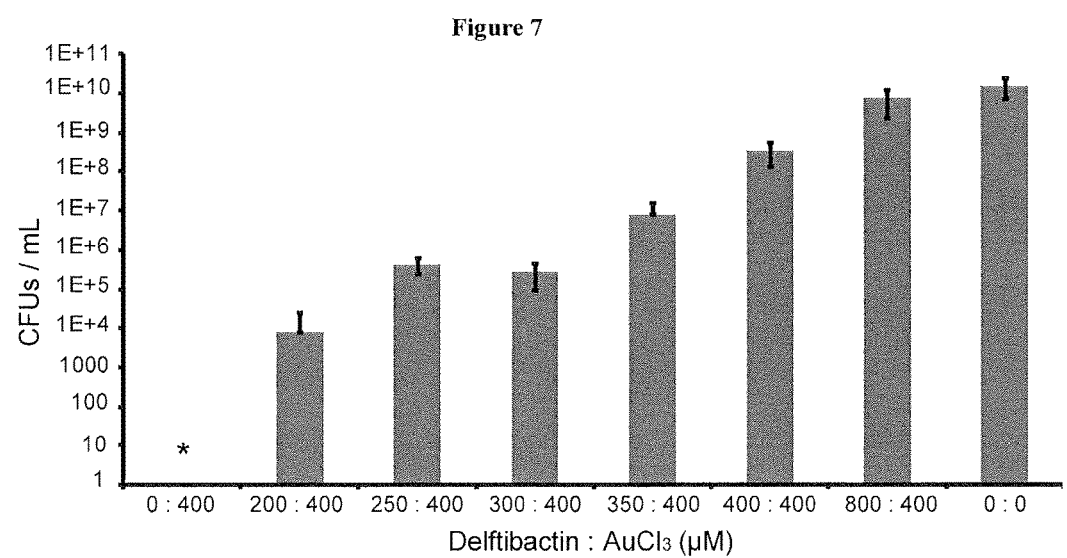
FIG. 7 is a bar graph showing the *Delfiia acidovorans* colony forming units (CFUs) after exposure to 400 μM $AuCl_3$ for 30 minutes. Delftibactin A was added to $AuCl_3$ solutions as indicated before exposing to *D. acidovorans*. *No survival was observed without the addition of delftibactin A. Results are shown as mean±s.d.; n=4.
Figure 8:
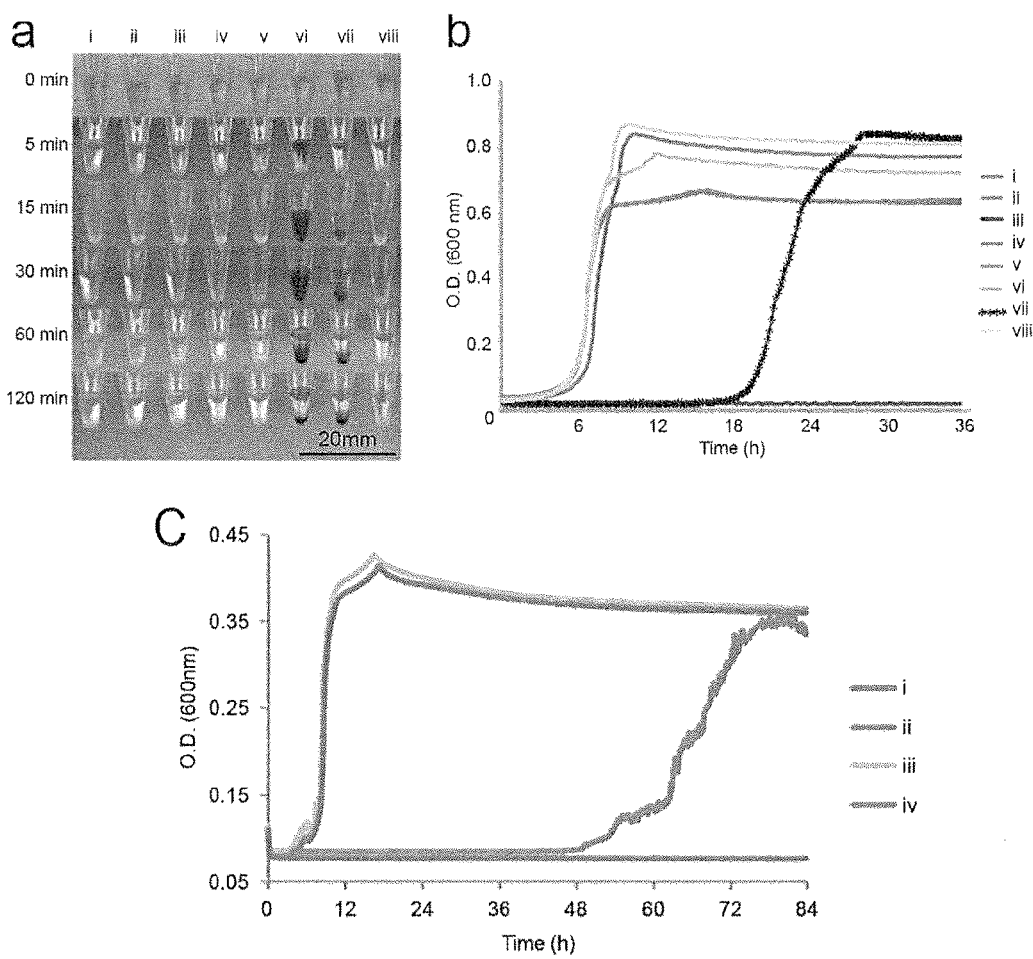
FIG. 8 shows (a) the time course progression of 5 mM $AuCl_3$ reacted with: i) water only ii) 5 mM delftibactin A iii) 5 mM $AuCl_3$ iv) 5 mM $FeCl_3$ v) 5 mM $AuCl_3$+5 mM $FeCl_3$ vi) 5 mM delftibactin A+5 mM $AuCl_3$ vii) delftibactin A+5 mM $AuCl_3$+5 mM $FeCl_3$ and viii) delftibactin A+5 mM $FeCl_3$; (b) growth curves of *D. acidovorans* ΔdelG in the presence of each reaction mixture shown in (a) at a final concentration of 30 μM in ACM. Results are a mean of three growth curves for each condition from a single representative experiment; and c) growth curves of *D. acidovorans* ΔdelG cultures inoculated 1:1000 into ACM followed by the addition of delftibactin A and/or gold as follows: i) 100 μM delftibactin A+10 μM $AuCl_3$, ii) 10 μM $AuCl_3$ only, iii) 10 μM delftibactin A only, and iv) water only. Results are a mean of three growth curves for each condition from a single representative experiment.

Purified delftibactin A was observed to co-precipitate with gold from solution, recapitulating the original findings in end-point assays (FIGS. 5a, b and c). It remained to be determined whether the gold precipitation caused by delftibactin A confers a protective advantage to *D. acidovorans* and assists in ameliorating gold toxicity. In initial assays this was addressed with an acute toxic exposure of the wild-type and the ΔdelG strains, whereby broth cultures of each were exposed for thirty minutes and the CFUs were subsequently determined. The results of this showed that a 102.8 fold increase in sensitivity to gold toxicity could be observed in the ΔdelG strain, and that this could be rescued with exogenous addition of purified delftibactin (FIG. 6). A detoxifying effect was observed in dose escalations of delftibactin to overtly toxic concentrations of $AuCl_3$ (FIG. 7), and subsequent examination revealed that while soluble gold is toxic at 10 μM, the blackened precipitate did not display any obvious toxicity when supplied in excess of 10 mM. Metals found within secondary gold deposits have been outlined previously (Reith et al., 2010), specifically revealing that the concentration of iron is low relative to gold. However, the fate of delftibactin A was probed when presented with equimolar concentrations of soluble gold and iron. This simultaneous exposure revealed that gold precipitation would proceed in the presence of high concentrations of iron (FIG. 8a). To assess what impacts this precipitation would have on *D. acidovorans* viability, cultures of the ΔdelG strain were set up containing the resultant gold reactions. Growth curves demonstrate that while iron-free conditions are optimal for detoxification due to metal competition, sufficient levels of detoxification occur in the presence of iron to support the growth of *D. acidovorans* (FIG. 8b). Chronic exposures were also tested, demonstrating that exogenous delftibactin A addition to cultures of the ΔdelG strain was sufficient to overcome chronic gold toxicity (FIG. 8c). The results of these experiments, though not in their natural context, inform on the protective nature of delftibactin A for *D. acidovorans*.

Figure 9:
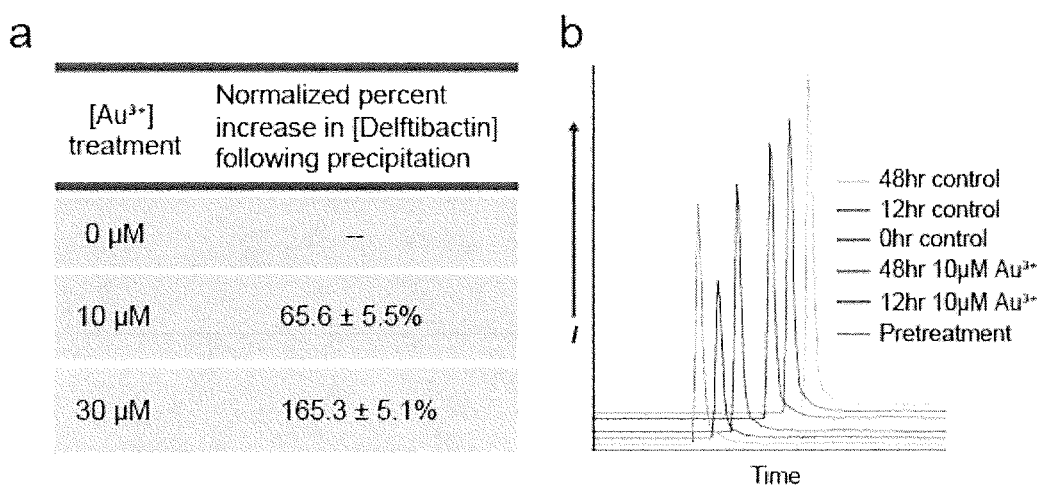
FIG. 9 shows (a) MRM-LCMS quantification of delftibactin A concentrations in response to gold concentrations. Values represent the percent increase in delftibactin A concentrations following precipitation by $AuCl_3$, normalized to an untreated control, ±propagated error; n=6; and (b) Sample MRM-LCMS chromatogram of (a).

Next, an experiment was performed, aimed at revealing whether *D. acidovorans* may maintain protective extracellular concentrations of delftibactin A by monitoring the loss of delftibactin A by gold co-precipitation, leading to an increase in delftibactin A production through a positive feedback mechanism (Miller et al., 2010). *D. acidovorans* supernatants treated with 10 and 30 μM $AuCl_3$ caused delftibactin A depletion, resulting in a compensatory increase in delftibactin A concentrations compared to an untreated control, representing a form of reactive homeostasis (FIG. 9). Delftibactin A concentrations were also responsive to iron concentrations, but in an inverse manner (Table 3), suggesting that delftibactin A is not regulated in the same way as a typical siderophore despite the presence of relevant genes in the delftibactin A cluster.

Figure 10:
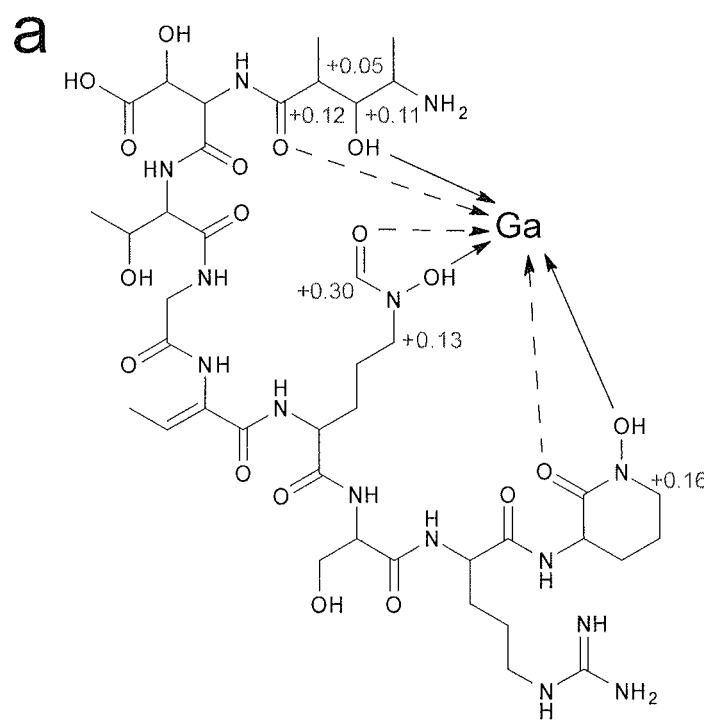
FIG. 10 is a schematic depicting the single metal binding site of delftibactin A as confirmed by gallium NMR.
Figure 11:
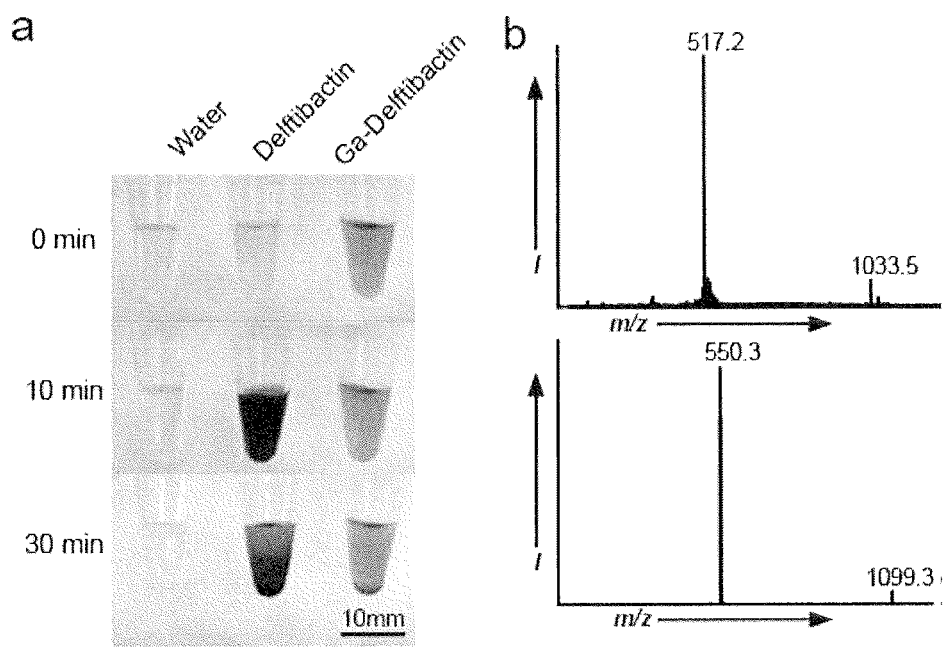
FIG. 11 shows (a) pictures of reactions of delftibactin A (5 mM) and Ga-delftibactin A (5 mM) with equimolar concentrations of $AuCl_3$; and (b) Mass spectra of free (top) and gallium-bound delftibactin (bottom).

Metallophores are recognized to create complexes with metals and whether or not such complexation was part of the gold-delftibactin A interaction was investigated. As the gold-delftibactin A association leads to co-precipitation and formation of an insoluble material, it was examined how delftibactin A may bind metals using gallium. NMR analysis of the delftibactin-gallium complex showed the coordinating activity of delftibactin A. These results indicated the $N^\delta$-hydroxy-$N^\delta$-formylornithine, the polyketide-extended portion of the N-terminal alanine, and the cyclic $N^\delta$-hydroxyornithine form ligands for metal binding (FIG. 10). This complexation is relevant to gold, as purified Ga-delftibactin A exposed to gold showed significantly decreased precipitation and protection of delftibactin A from gold (FIG. 11).

Figure 12:
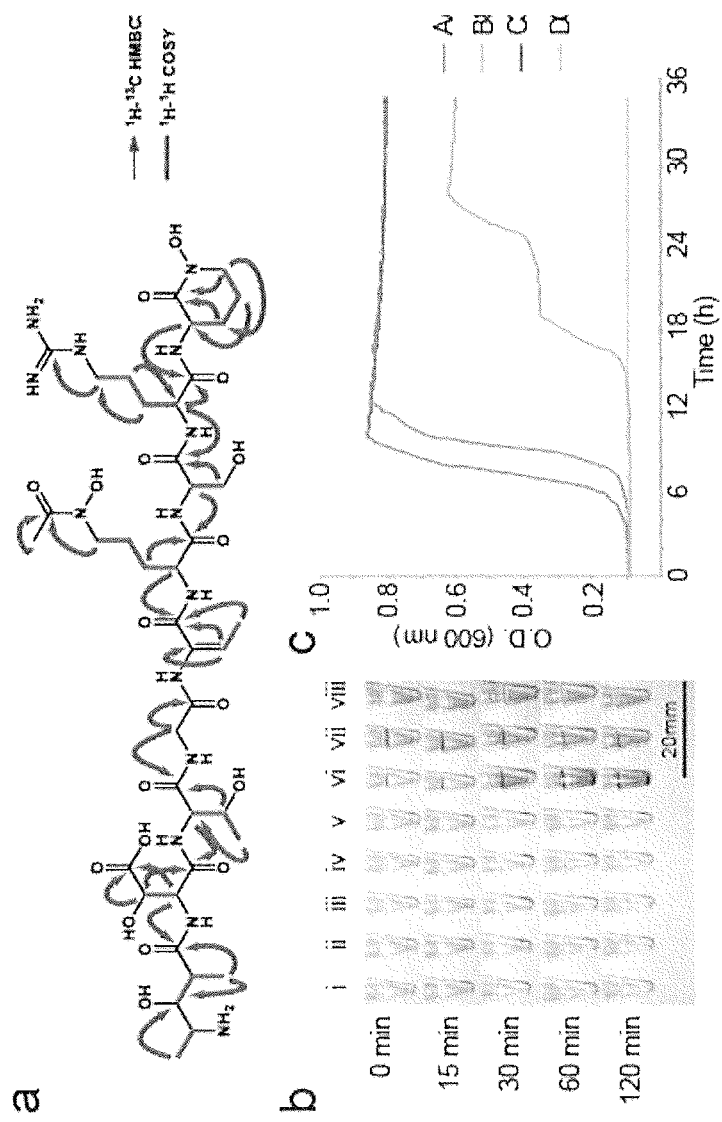
FIG. 12 shows (a) the structure of the acetylated analog and spin systems for $^1H$-$^{13}C$ HMBC, $^1H$-$^1H$ COSY and $^1H$-$^{15}N$ HMBC in $D_2O$ for delftibactin B (acetylated hydroxy-ornithine delftibactin A) in a further exemplary embodiment of the present application; b) pictures of reactions demonstrating $AuCl_3$ (5 mM) precipitation by delftibactin B over time in the absence and presence of $FeCl_3$ as follows: i) water only ii) 5 mM delftibactin B iii) 5 mM $AuCl_3$ iv) 5 mM $FeCl_3$ v) 5 mM $AuCl_3$+5 mM $FeCl_3$ vi) 5 mM delftibactin B+5 mM $AuCl_3$ vii) delftibactin B+5 mM $AuCl_3$+5 mM $FeCl_3$ viii) delftibactin B+5 mM $FeCl_3$; and (c) growth curves of *D. acidovorans* ΔdelG in the presence of reaction mixture of water (A), 125 μM $AuCl_3$ (B), 125 μM $AuCl_3$+125 μM delftibactin A (C), and 125 μM $AuCl_3$+125 μM delftibactin B (D) showing that delftibactin A (formylated) is more protective against $AuCl_3$ toxicity than delftibactin B (acetylated). Results are a mean of three growth curves for each condition from a single representative experiment.
Figure 13:
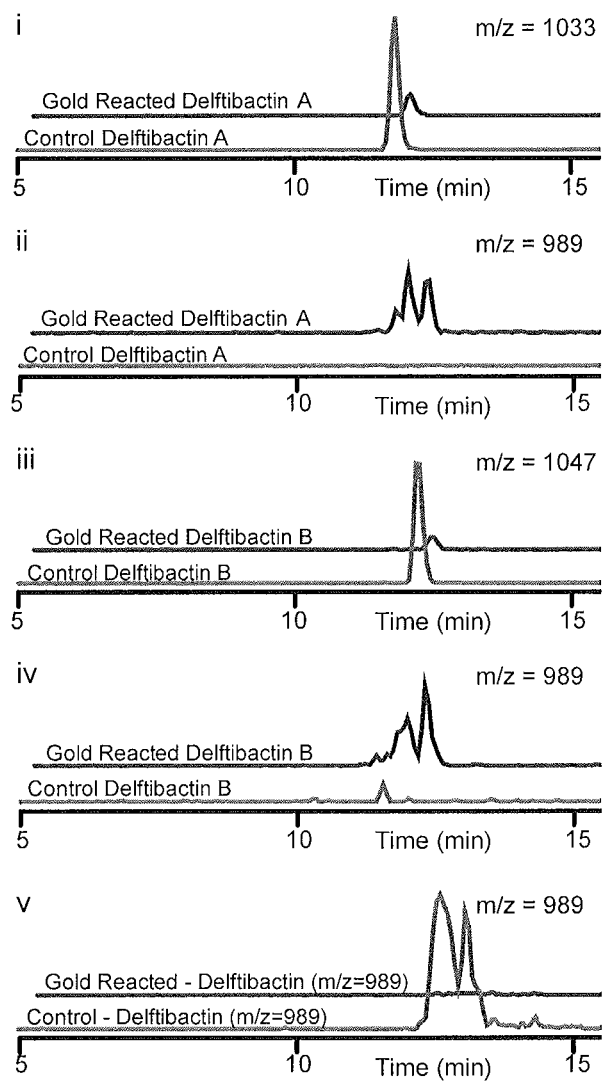
FIG. 13 shows the LC-MS chromatograms from the reaction of delftibactin A and delftibactin B with equimolar (5 mM) concentrations of $AuCl_3$. The reaction mixtures were compared with an unreacted control. Decrease in delftibactin A and B is shown after incubation with $AuCl_3$ and was accompanied by an increase in a new delftibactin species (m+/z=989 ion) (i-iv). Further reaction of the purified new delftibactin species with equimolar concentrations of $AuCl_3$ for 2 h shows a loss of the delftibactin intermediate from solution (v).
Figure 14:
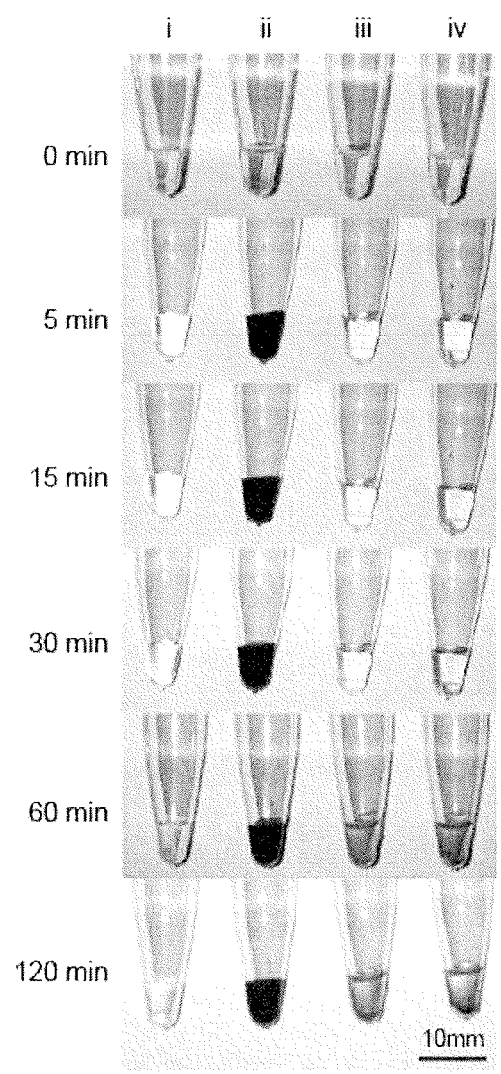
FIG. 14 shows pictures of the timecourse of 5 mM $AuCl_3$ reacted with i) water ii) 5 mM delftibactin A iii) 5 mM delftibactin-$AuCl_3$ reaction product and iv) 5 mM delftibactin B monitored over 2 h for $AuCl_3$ precipitation. The results demonstrate that all delftibactin species eventually co-precipitate with $AuCl_3$.
Figure 15:
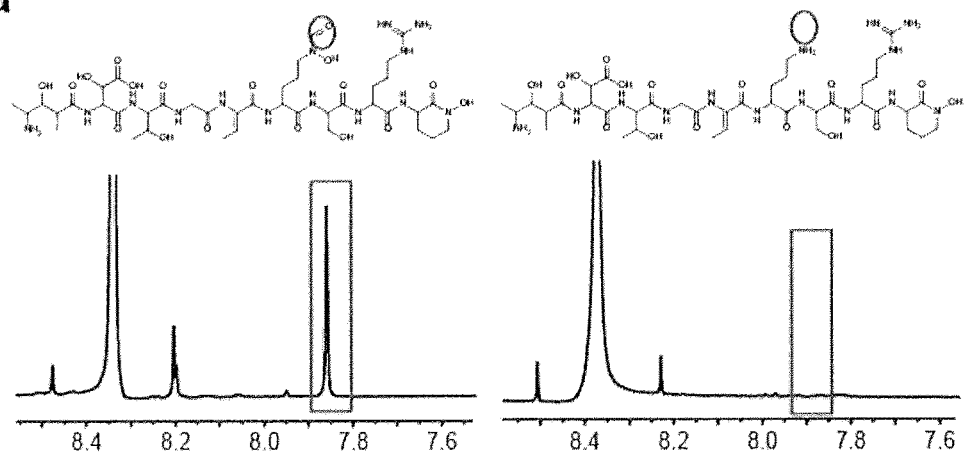
FIG. 15 shows (a) the aromatic region of $^1D$ proton NMR of delftibactin A (left) and the reacted delftibactin intermediate (m+/z=989) (right). The formyl hydrogen signal is absent in the m+/z=989 delftibactin intermediate; (b) fragmentation of the double charged ion of the reacted delftibactin species (m+/z=989) with diagnostic fragments shown. Mass loss of 44 is localized to ornithine functional group; and (c) the final structure of transient delftibactin-$AuCl_3$ reaction intermediate. Structure and mass deviation is consistent with the loss of the formyl and hydroxyl group from ornithine.
Figure 15:
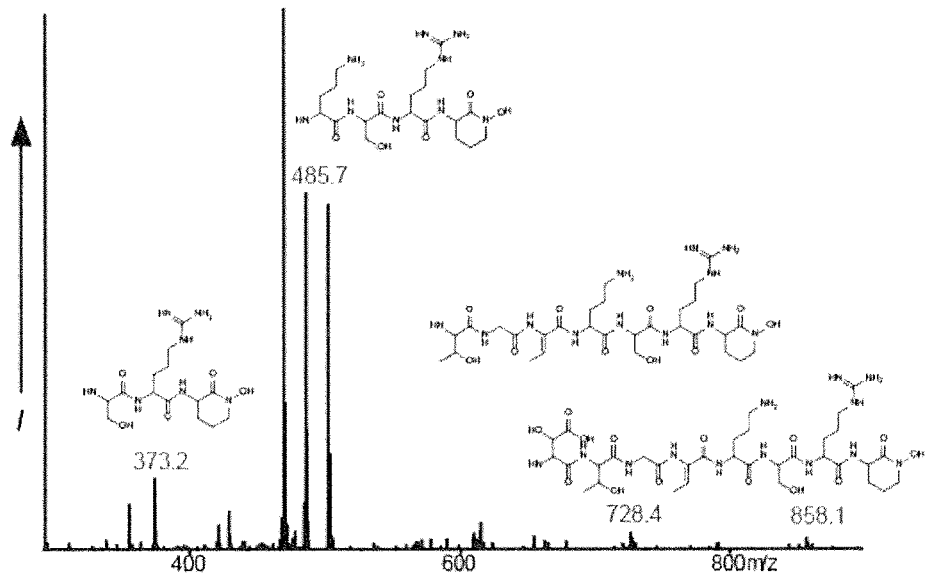
Figure 15:
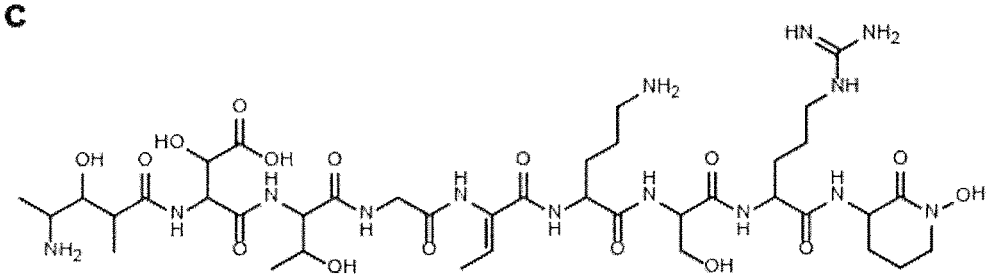
Figure 16:
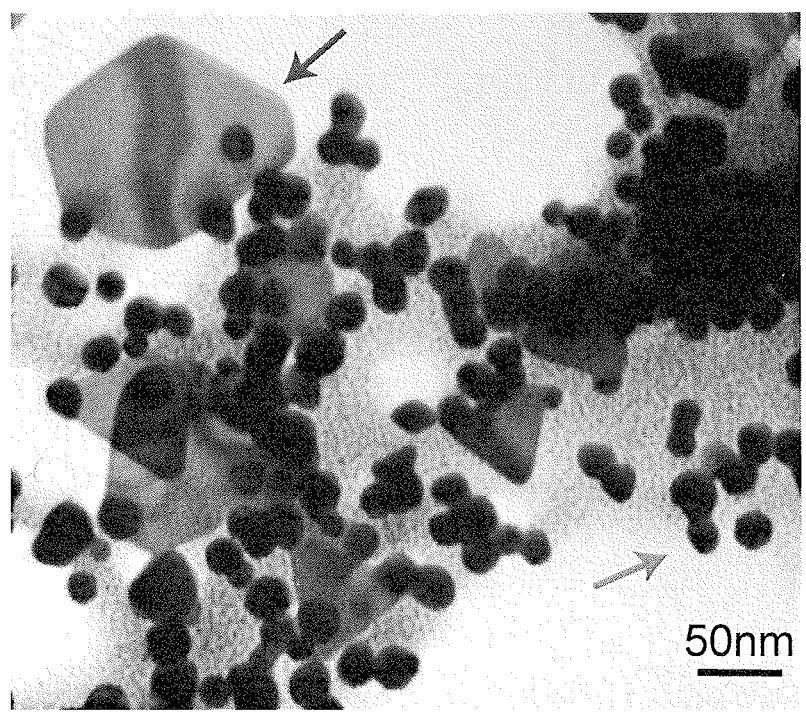
FIG. 16 shows transmission electron microscopy of delftibactin A-gold (2:1) complex after 10 minutes and reveals the presence of colloidal and octahedral gold nanoparticles, reminiscent of those seen in natural deposits. Darker arrows indicate colloidal gold. Lighter arrows indicate octahedral gold.
Figure 17:
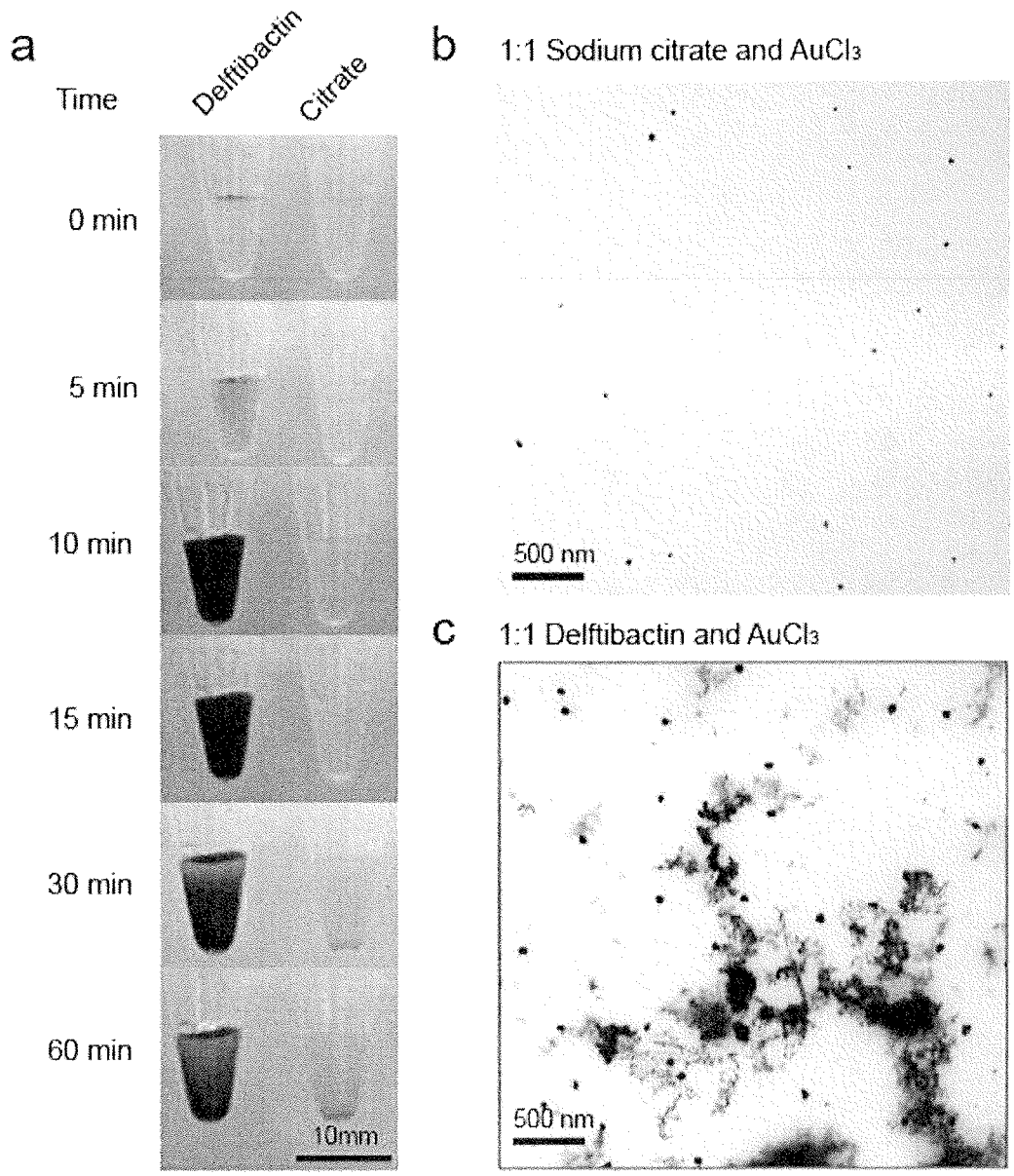
FIG. 17 shows (a) pictures of the reaction of $AuCl_3$ (5 mM) with equimolar concentrations of delftibactin A or sodium citrate showing that delftibactin A rapidly forms complex precipitates of gold nanoparticles; (b) TEM images of the sodium citrate-gold reaction after 10 minutes; and (c) TEM images of the delftibactin-gold reaction after 10 minutes.

Although the gallium/gold competition may inform on how gold interacts with delftibactin A direct evidence of gold binding by delftibactin was investigated next. An initial gold-delftibactin A complex was identified through mass spectrometry and its identity was confirmed through diagnostic MS/MS fragmentation. Natural delftibactin A variants were used to reveal in more depth the mechanisms that lead to gold precipitation and which sites within delftibactin A are associated with gold complexation. Several compounds were observed to elute at a similar time as delftibactin A, and had comparable fragmentation patterns and masses, indicating that they may be structural analogues which may be useful if they possessed modifications within the proposed chelation core. One promising candidate was identified and subsequently characterized, bearing a hydroxylated and acetylated ornithine (delftibactin B, m+/z=1047; FIG. 12a). Subsequent examination of the complexing properties and protective nature of delftibactin B indicated that it was less efficient in gold reduction (FIG. 12b), resulting in decreased detoxification (FIG. 12c). Exposing delftibactin A and delftibactin B to $AuCl_3$ leads to their depletion, however, new peaks emerge following the exposure, the predominant one corresponding to an m+/z=989 (FIG. 13), which continues to react with gold and also is lost from solution (FIG. 13 and FIG. 14). Structural characterization indicates this reaction product does not bear the ornithine modifications observed in delftibactin A and B (FIG. 15), indicating that delftibactin A can chelate gold and also react with it. This likely explains why delftibactin B is less protective, as it has a ketone moiety that is less easily oxidized than the aldehyde found on delftibactin A, which may be partially responsible for gold reduction. Transmission electron microscopy was used to better assess the nature of the gold precipitate and revealed an abundance of colloidal gold nanoparticles and octahedral gold platelets (FIG. 16). Such solid gold forms are authentic morphologies found in gold nuggets and bacterioform gold (Reith et al., 2007; Hough et al., 2008). These data show that pure delftibactin A is capable of creating naturally occurring complex gold structures from $Au^{3+}$ on short timescales (seconds), at room temperature, neutral pH, and at rates that far exceed those observed for traditional gold nanoparticle producing agents such as citrate (Ojea-Jimenez et al., 2010) (FIG. 17), providing a potential mechanism for bacterial gold biomineralization. While not wishing to be limited by theory, it is proposed that delftibactin A facilitates this biomineralization and protects *D. acidovorans* by chelating soluble $Au^{3+}$ and directly precipitating as a complex, or by binding and reducing gold through oxidative decarboxylation before chelating a second $Au^{3+}$ ion and precipitating as a complex.

Collectively, these results indicate that although delftibactin A is dispensable in culture, consistent with other secondary metabolites, it plays an important role in protecting its gold-resident producer from toxic soluble gold. Further, this Example shows that gold biomineralization can take place through the secretion of this metallophore from gold-resident bacteria. This phenomena echoes situations observed previously including boron chelation by vibroferrin (Amin et al., 2007), and copper chelation by yersiniabactin (Chaturvedi et al., 2012) and methanobactin (Kim et al., 2004), wherein bacterial siderophores have dual physiological roles that are important in their environments. Delftibactin A appears to be the first example of a co-opted metallophore that protects its producer from toxic soluble gold and provides a mechanism for bacterial gold biomineralization.

Example 2: Delftibactin-Like Metabolites from Other Organisms

Example 1 discloses metabolites of *D. acidovorans*, delftibactin A and B, which act to extact gold from solution (Johnston et al., 2013). As compared to citrate—the industrially used agent for creating gold nanoparticles—delftibactin A does not need to be heated with the gold-containing sample. Further, the time frame in which the soluble gold is reduced and coalesced as nanoparticles is much faster.

Delftibactin A also shows considerable promise in the bio-remediation of toxic soluble gold, as the reduced nanoparticles formed by delftibactin A are—like delftibactin A itself—nontoxic, and are formed as part of a complex matrix, that would involve considerably less liquid handling. Further, many commercially available methods for removing soluble gold, including the use of activated carbon or ionic-exchange resins, are non-specific, and may result in enrichment for other contaminating metals. Delftibactin A is specific for a small set of metal ions including iron, gallium, and most notably gold, and is a considerable improvement on currently available methods of remediation.

A group of delftibactin-like compounds are described in the present Example. These microbial compounds were targeted for isolation using a method coined 'genome mining', whereby the genes that encode the enzymes required for producing delftibactin A were used as the query in a BLAST search to identify similar gene clusters that exist in other organisms. A delftibactin gene cluster analysis is shown in Table 4. Using this methodology, two genera were identified that contained delftibactin-like gene clusters: *Variovorax* and Acidovorax. Organisms containing similar gene clusters were subsequently fermented and 9 delftibactin-like compounds were isolated.

Disclosed in this Example are bacterial metabolites of the chemical scaffolds shown in FIG. 18. These metabolites are cyclic non-ribosomal peptides, with chemical moieties consistent with the delftibactin family and other metallophores. The metabolites are predicted to have delftibactin A like properties, namely the ability to obtain solid gold from the environment or chemical and industrial processes.
Results The biosynthetic genes encoding the delftibactin A non-ribosomal peptide synthetase (NRPS) were used to probe the GenBank database and identify related biosynthetic loci from other organisms. These biosynthetic gene homology searches revealed a series of undescribed NRPSs from organisms including: Acidovorax (*A. citrulli* AAC00-1) and *Variovorax* (*V. paradoxus* S110 and *V. paradoxus* EPS). FIG. 19 demonstrates the high genetic similarity between the delftibactin A biosynthetic gene cluster and those found in *Variovorax* and Acidovorax using Mauve alignment software. The highly similar gene clusters indicate their final products would also be likewise related. Using this as a guide, these organisms were obtained and fermented for delftibactin A-like molecules (shown in FIG. 18).

To isolate putative metabolites, *A. citrulli* AAC00-1 and *V. paradoxus* S110 were grown in Acidovorax Complete Media (ACM), the same media used for delftibactin A production. After 3 days of growth at 30° C., Acidobactin A and B and Vacidobactin A and B were isolated. These structures were determined by mass spectra (MS) analysis and nuclear magnetic resonance (NMR) experiments. Acidobactin C could be identified within the extract by its similar fragmentation pattern to acidobactin A and B and subsequent tandem MS analysis revealed its structure.

An environmental isolate obtained from Cootes Paradise, near McMaster University, was determined to be a strain of *V. paradoxus* by 16S gene sequencing. Subsequent fermentation of this strain in Chitinophaga Defined Media showed the production of Variobactin A-E. Variobactin A's structure was determined by MS and NMR experiments. Variobactin B-E's structures were determined using MS fragmentation analysis.

From these fermentations, two related chemical cores have been identified that are related to the gold-complexing compound, delftibactin A. These cores have common chemical moieties found in delftibactin A, including formylated, acetylated, hydroxylated ornithines, serines, threonines, and beta-hydroxy aspartic acids. In addition, a common polyketide extension is found in all cores.

The homology between these metabolites and delftibactin A predicts they have activity in extracting soluble gold out of solution and/or forming gold nanoparticles and solid gold. Indeed, when exposed to gold, acidobactin A has shown the gold complexing phenomenon. Due to the high similarity of the other compounds, it can be deduced that other molecules with these cores that are related to delftibactin A would also have similar gold activities.

Example 3: Test Strips for Gold Analysis

Figure 20:
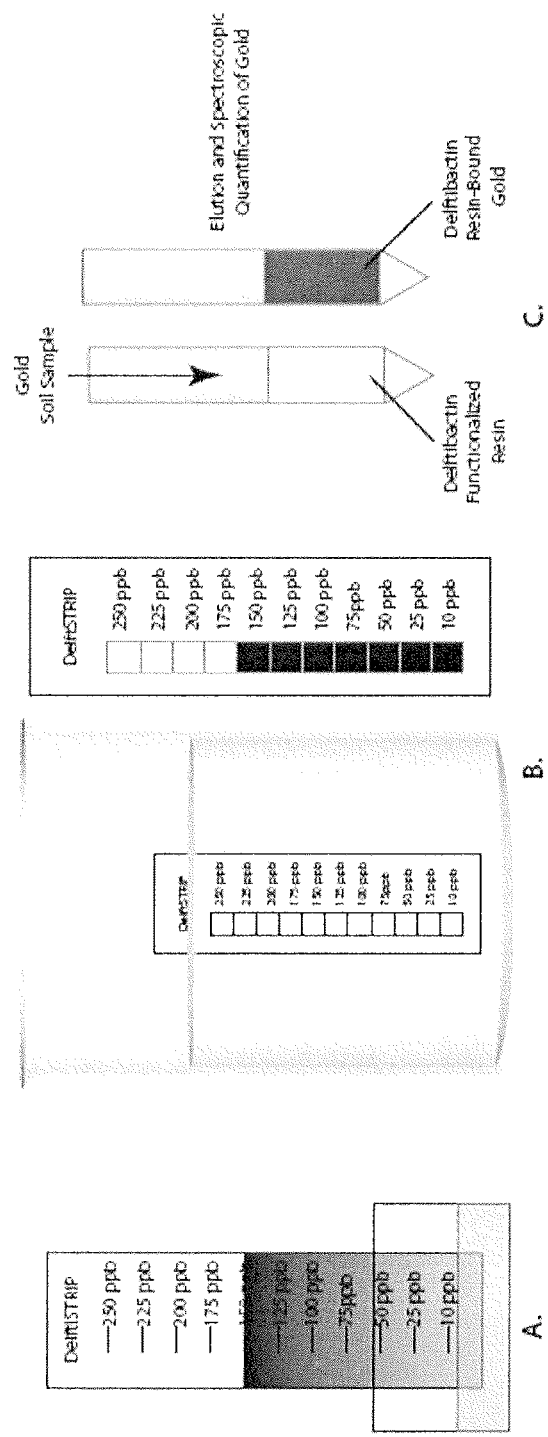
FIG. 20 is schematic showing several exemplary embodiments for how the metallophores of the application can be used as a biosensor of gold. (A) thin layer chromatography concept. (B) strip concept. (C) column quantification concept.

FIG. 20 shows several ways by which the metallophores of the application are used as a detector of gold. In a first embodiment, the detector is based on a thin layer chromatography concept, for example as shown in FIG. 20A. In this embodiment, a concentration gradient of one or more of the metallophores of the application is absorbed onto a test strip and is used to determine the concentration of gold in a solution after fixed incubation period. This occurs whereby solutions with low concentrations of gold will be captured lower on the strip by the metallophores of the application as the liquid moves upwards and solutions with high concentrations of gold ions will saturate the metallophore of the application lower on the strip and move higher creating a higher band of compound-induced blackening. In a second embodiment, a test strip comprising one or more of the metallophores of the application absorbed thereto is submerged in liquid sample to determine gold concentration, for example as shown in FIG. 20B. Varying the ratio of the compound(s) to gold causes differential darkening, allowing for easy quantification and detection of gold from a solution. In a third embodiment, one or more of the metallophores of the application are absorbed within a chromatographic column to provide a similar colorimetric indication as the submerged test strip. This embodiment advantageously allows for increased sample volumes to be used, which can increase the signal (blackening) or decrease the limit of detection within a sample (see for example, FIG. 20C).

Figure 21:
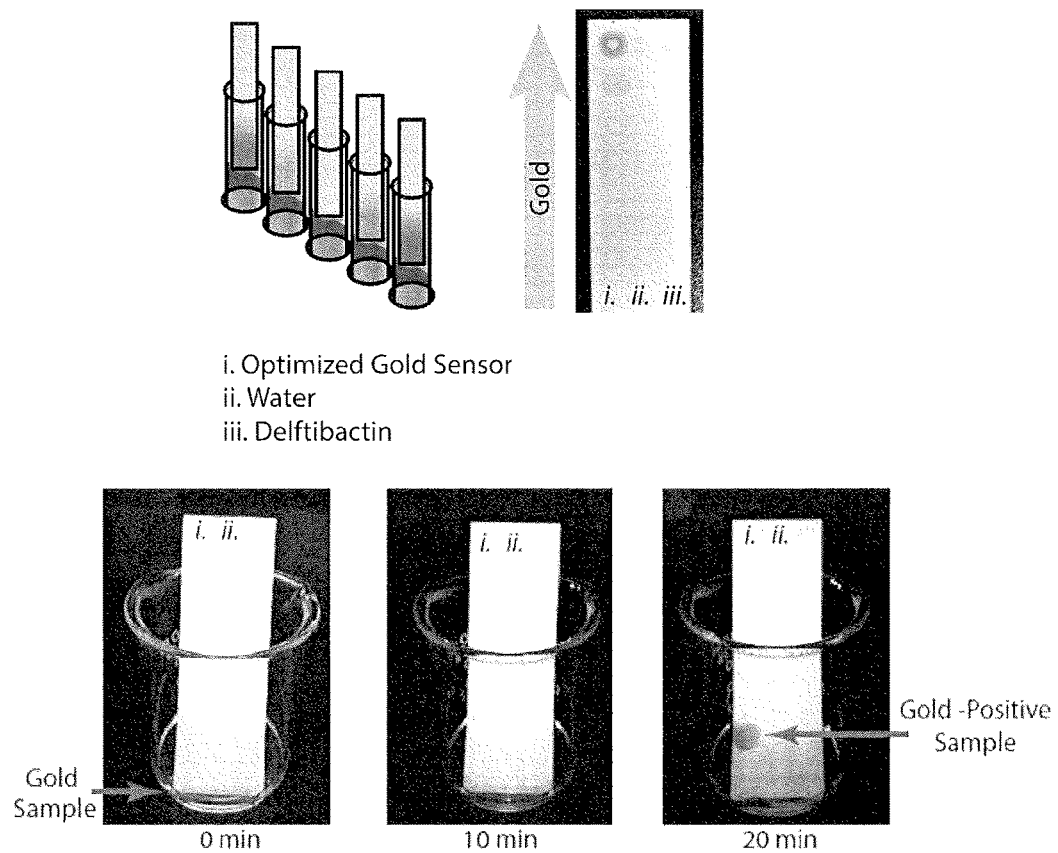
FIG. 21 shows schematics of test strip development as exemplary embodiments delftibactin A (iii) and enterobactin (a known metallophore) (i) were applied in increasing concentrations to a C18 thin layer chromatography (TLC) plate and a 1 mL sample of 1 mM $AuCl_3$ was overlayed and allowed to react. The picture at the top of the figure was taken after 10 min. The picture at the bottom of the figure show delftibactin A immobilized on a C-18 thin layer chromatography slide and a solution containing gold chloride was used to develop the strip. Pictures were taken at the times indicated. Characteristic darkening can be seen where immobilized delftibactin A reacts with gold in the sample.

As shown in FIG. 21, delftibactin A (iii) and enterobactin (a known metallophore) (i) were applied in increasing concentrations to a C18-silica thin layer chromatography (TLC) plate and a 1 mL sample of 1 mM $AuCl_3$ was overlayed and allowed to react. Pictures were taken after 10 min.

Further, as shown in FIG. 21, delftibactin A was immobilized on a C18-silica thin layer chromatography slide. A solution containing gold chloride was used to develop the strip. Pictures were taken at the times indicated. Chararacteristic darkening can be seen where immobilized delftibactin A reacts with gold in the sample.

Example 4: Are Other Microbial and Synthetic Metallophores Capable of Forming Ordered Gold Nanoparticles Materials and Methods
Isolation of Siderophores Delftibactin A and B were isolated as described in Example 1. Enterobactin, aerobactin and yersiniabactin were isolated from *Escherichia coli* Nissle 1917 (Mutaflor). *Escherichia coli* Nissle 1917 was isolated from a single capsule of Mutafluor on a Luria-Bertani agar plate. 6×1.5 L of *Escherichia coli* Nissle 1917 (innoculated from a single colony) was grown for 3 days at 37° C. at 200 rpm in Fernbach flasks containing M9 media supplemented with 0.5% glycerol and 0.5% glucose. Resin was added (HP20, DIAION), and shaken with cultures for 2 hours. Resin was collected by filtration and extracted 4 times with 500 mL of methanol. The dried extract was separated using a Combiflash (Isco) medium pressure liquid chromatography system using a 24 g RediSep (Isco) silica column. The extract was separated stepwise into seven 150 mL fractions using methanol and dichloromethane with the following methanol concentrations: 5, 15, 25, 35, 50, 70, and 100% for each fraction respectively. Fraction 1 contained yersiniabactin. Fraction 3 contained enterobactin. Fraction 7 contained aerobactin. Compounds were further purified by high performance liquid chromatography (HPLC)(Dionex) using a Luna C18 250 mm×15 mm semi preparative column (Phenomenex) and analyzed by mass spectrometry (Bruker, AmazonX). All methods used a flow rate of 8 mL/min. The solvents were water+0.1% formic acid (FA) and acetonitrile (ACN)+0.1% FA. For yersiniabactin and enterobactin the mobile phase was linear from 10% ACN at 5 minutes to 80% ACN at 32 min. Yersiniabactin eluted at 25.64 min (m/z=482.0). Enterobactin eluted at 22.68 min (m/z=670.0). For aerobactin, the mobile phase was linear from 2% ACN at 5 min to 100% ACN at 24 min. Aerobactin eluted at 15.08 min (m/z=565). Siderophore structures were confirmed by mass and fragmentation patterns compared to literature values (Berner et al., 1991; Chaturvedi et al., 2012; Henderson et al., 2009; Lin et al., 2005).

Gold-Siderophore Reactions

Stock solutions of containing 10 mM of each siderophore, 10 mM EDTA, 10 mM bipyridyl (Sigma), 10 mM $AuCl_3$ (Sigma) and 10 mM $FeCl_3$ were made. Ten microliters of the $AuCl_3$ stock solution was aliquoted into separate 200 µL microcentrifuge tubes, followed by the addition of 10 µL of each respective siderophore or metal chelator, where water was used as a control. The reaction was monitored over time and images were taken. After 2 h, a sample of the mixture was diluted 10× and analyzed by transmission electron microscopy (TEM) (see below). The remaining sample was centrifuged at 13,000 rpm for ten minutes. A 10 µL sample of the supernatant was diluted in 90 µL of water and subsequently analyzed by LC-MS. A control of unreacted siderophore and metal chelator of the same concentration was also analyzed for comparison. For gold-iron competition assays, 5 µL of $AuCl_3$ and 5 µL of $FeCl_3$ were added similarly to each 200 µL microcentrifuge tube, followed by the addition of 10 µL of the stock siderophore and metal chelator solutions. Reactions were monitored similarly. UV-vis spectrums were obtained using a Synergy 4 microplate reader (Biotek).

TEM Imaging

Transmission electron microscopy imaging was performed with a JEOL JEM 1299 EX TEMSCAN transmission electron microscope (JEOL, Peabody, Mass., USA) operated at an accelerating voltage of 80 kV. Sample preparation: a 2 µL drop of a diluted (10×) siderophore-gold reaction was deposited over a formvar-coated TEM grid, and was allowed to dry under ambient conditions before being imaged. Gold nanoparticle size distribution was determined using the software, ImageJ.

Results and Discussion

Figure 22:
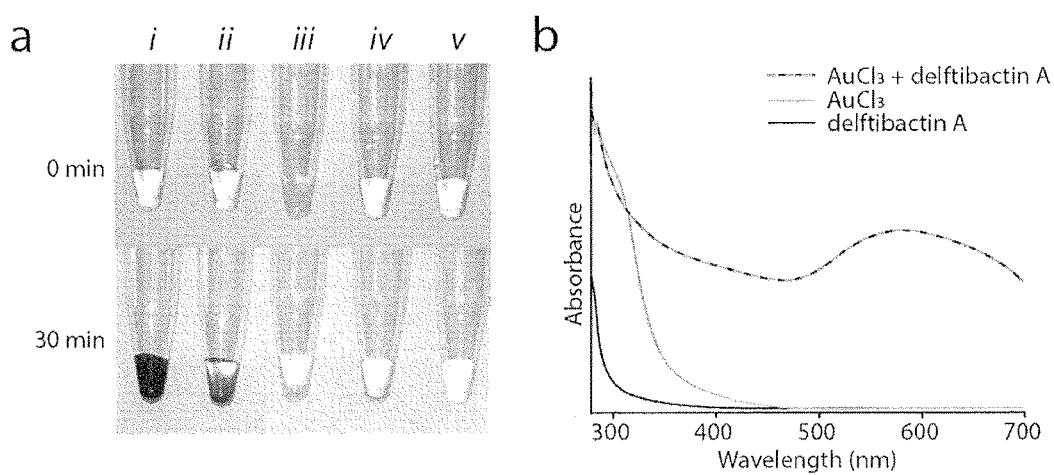
FIG. 22 shows (a) gold nanoparticle formation by delftibactins and commercial chelators. A solution of 10 mM $AuCl_3$ was reacted with equimolar concentrations of delftibactin A (i), delftibactin B (ii), EDTA (iii), bipyridyl (iv), and water (v); and (b) UV-vis spectrum of 5 μM delftibactin, 5 μM $AuCl_3$, and equimolar concentrations of reacted delftibactin A and $AuCl_3$ after 15 min.

There are many natural and industrial used metallophores that interact with metals using specific chemical mechanisms. Most of these compounds have not been assayed for the capacity to create gold nanoparticles or direct nanoparticle formation, however, there is evidence that secreted microbial products cause gold nanoparticle formation (Malhotra et al., 2013). By examining several classes of synthetic and naturally occurring metallophores, classes that can be employed to direct gold nanoparticle assembly can be identified along with the role natural metallophores may play in gold biomineralization. As a first evaluation, the gold nanoparticle forming capacity of delftibactin was compared to chelating substances of a non-natural origin, including common commercial metal chelators ethylenediaminetetraacetic acid (EDTA) and bipyridyl. Visual inspection of chelator-$Au^{3+}$ reaction mixtures revealed that while delftibactin A and B solutions rapidly undergo a characteristic blackening and an increase in absorbance at 600 nm within the UV/Vis spectrum indicative of gold nanoparticle formation, synthetic chelating agents fail to develop a similar effect even after prolonged exposure to gold ions (FIG. 22). This suggests the chelation moieties found in delftibactin A and B and other microbial metallophores may be important for this phenomenon and based on previous studies into the mechanism of gold complexation by delftibactin, it is suggested that the N-formylated hydroxy ornithine found in the chelation core is of particular importance for gold nanoparticle formation by delftibactin A and B.

Figure 23:
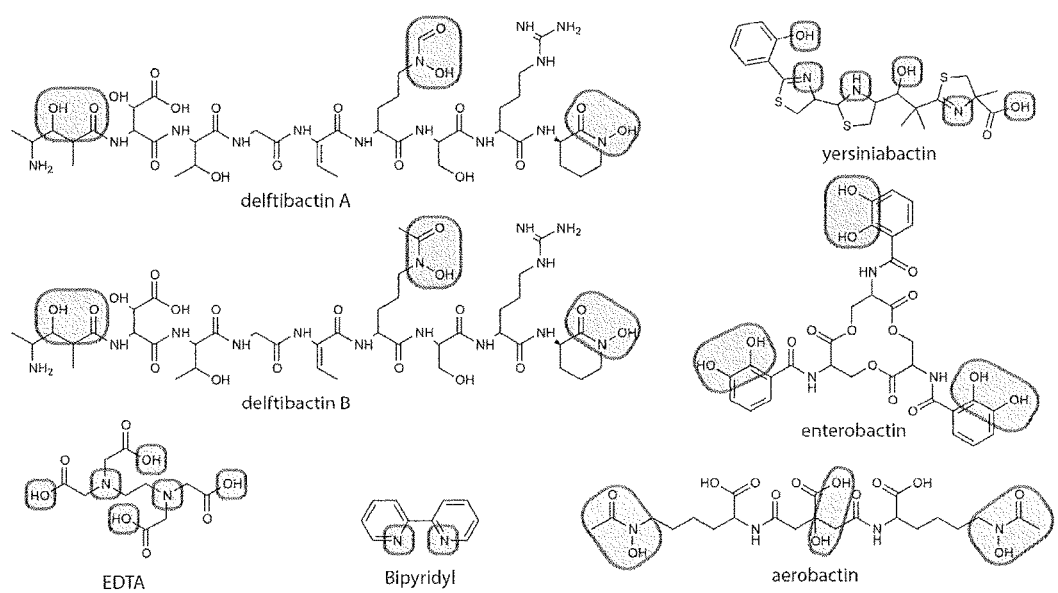
FIG. 23 shows the structures of various metallophores examined for gold nanoparticle formation properties. Major classes of metallophore compounds are shown: hydroxamate-type (delftibactin, A, B, aerobactin), catechol-type (enterobactin), thiazoline-type (yersiniabactin), citric acid-type (aerobactin), and commercial chelators (EDTA, bipyridyl). Areas involved in metal complexation are highlighted.
Figure 24:
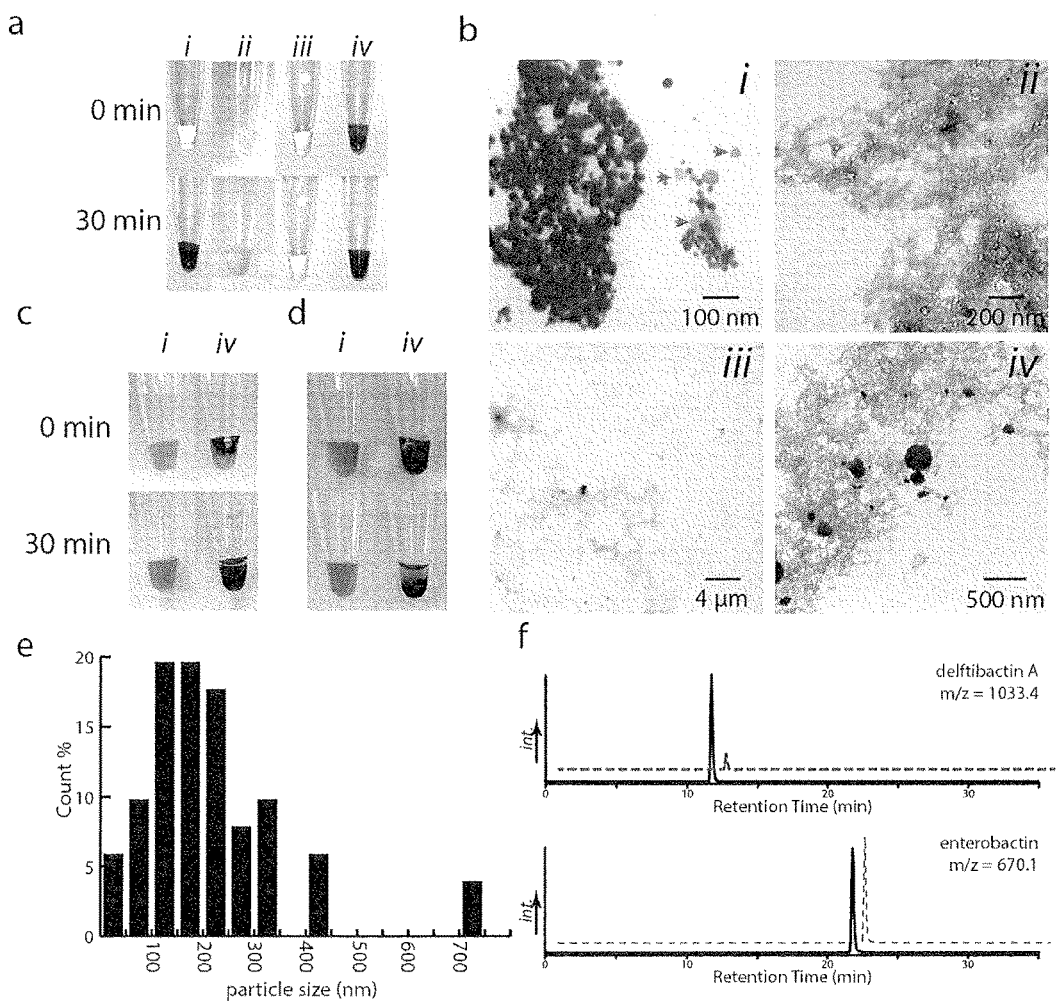
FIG. 24 shows (a) pictures of the reaction of a solution of 10 mM $AuCl_3$ with equimolar concentrations of delftibactin A (i), yersiniabactin (ii), aerobactin (iii), and enterobactin (iv) leading to gold nanoparticle formation; (b) transmission electron microscope images of the reactions in (a); (c) pictures of the reaction of (i) delftibactin A and (iv) enterobactin with equimolar concentrations of $AuCl_3$ and $FeCl_3$. Pictures were taken at 0 minutes and 30 minutes; (d) pictures of the reaction of (i) delftibactin A and (iv) enterobactin with $AuCl_3$ after pre-exposure of the peptide with equimolar concentrations of $FeCl_3$. Pictures were taken at 0 minutes and 30 minutes; (e) colloidal gold nanoparticle distribution pattern for delftibactin A; and (f) extracted ion chromatograms of delftibactin A and enterobactin after 2 hr exposure to $AuCl_3$ (dotted line). Unreacted controls are shown as a solid line.
Figure 4:
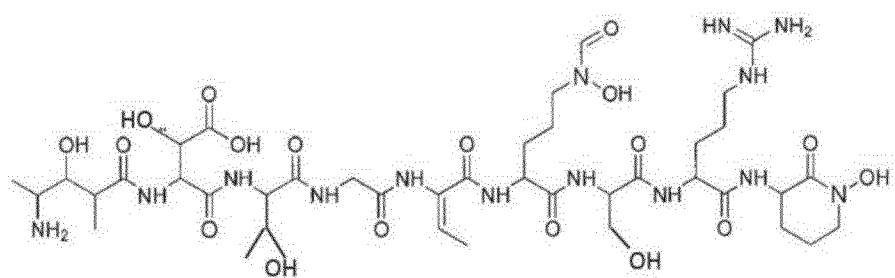

To investigate whether other microbial metallophores are capable of forming ordered gold nanoparticles, members of different structural classes were isolated, including hydroxamates, catechols, citrates, and mixed-ligands. Metallophores were isolated from the human-associated probiotic bacterium *Escherichia coli* Nissle 1917, which is used to prevent and treat several gastrointestinal disorders and overproduces a variety of metallophores including enterobactin (catechol), salmochelin (catechol), aerobactin (hydroxamate and citrate), and yersiniabactin (mixed-ligand) (FIG. 23) (Valdebenito et al., 2006). Considering that sulphur commonly reacts with gold in the environment and the dual role yersiniabactin plays in copper and iron binding, it was suspected that yersiniabactin could also functions as a gold reducing agent in vitro (Lengke et al., 2011). Repeating the gold complexation assay with yersiniabactin demonstrated that it does not generate substantial quantities of gold nanoparticles, suggesting that it cannot effectively reduce $AuCl_3$ (FIG. 24a).

The hydroxamate metallophore aerobactin, which is biosynthesized from lysine and the known gold nanoparticle forming agent citric acid, was also tested. Previous work suggests that aerobactin may also be a successful gold complexing and reducing agent due to the presence of an N-acetylation as part of the hydroxamate moiety—an important feature in the delftibactin A and B chelation core. However, analysis of gold complexation assays demonstrates that aerobactin reactions fail to produce defined gold nanoparticles (FIG. 24a). Finally, gold complexation assays were performed with the catechol siderophore enterobactin, which has the highest iron affinity of all siderophores studied to date. Enterobactin reactions showed considerable gold nanoparticle formation (FIG. 24a).

A closer analysis of the reaction mixtures using transmission electron microscopy (TEM, FIG. 24b), revealed that the colloidal nanoparticles produced by delftibactin A are more defined, and range in size from 10.6 to 712 nm with an average particle size of 211.2 nm as compared to the nanoparticles produced by yersiniabactin, which did not create any distinct nanoparticles. The colloidal nanoparticle distribution pattern for delftibactin A is shown in FIG. 24e. Enterobactin, generated particles range from 26 nm to 339 nm in diameter, however, the majority of the blackening that occurred in the microcentrifuge tube is not related to the defined colloidal particles as demonstrated in the TEM image (FIG. 24b). In addition to colloidal nanoparticles, delftibactin A also produces octahedral gold particles, which are not formed by either of the other two metallophores reaching sizes greater than several micrometers in diameter. The quick reaction of enterobactin with $AuCl_3$ suggests there are time-dependent factors responsible for octahedral gold formation, where a slowed and directed complexation by the chelation core may allow for better growth of the larger, octahedral gold nanoparticles that are found in the nascent stages of gold nugget formation.

Typical bacterial metallophores and/or siderophores complex select metals with high affinity, but can ultimately release the metal for use in cellular processes through redox-mediated release (e.g. reduction of $Fe^{3+}$ to $Fe^{2+}$) and used again to sequester additional metal ions (Hider & Kong, 2010). While delftibactin A maintains its solubility when bound to iron, complexing to gold causes an abrupt and total loss of solubility, facilitating the removal of $Au^{3+}$ ions from solution and detoxifying the local environment. Delftibactin A and B possesses a single metal binding site, as a result iron-bound delftibactin A and B is less able to precipitate gold, and delftibactin-gold complexes are incapable of binding iron. In instances where apo-delftibactin encounters $Au^{3+}$ outside the cell before $Fe^{3+}$, delftibactin is depleted and can no longer sequester iron or protect from toxic gold ions. This is a fortuitous phenomenon for D. acidovorans as low iron concentrations in gold rich environments drive delftibactin production through iron regulatory mechanisms, which remain unsatisfied as delftibactin concentrations are continually depleted by the complexation, detoxification, and deposition of gold. This produces a chemical gradient that allows continuous production of a delftibactin shield against toxic gold ions (Johnston et al., 2013). To examine if enterobactin was also lost from solution after interaction with $Au^{3+}$, $AuCl_3$-enterobactin/delftibactin A reaction mixtures were monitored with LC-MS and compared to unreacted controls. As expected, the concentration of delftibactin A decreased after $AuCl_3$ exposure, however, the concentration of enterobactin remained unchanged suggesting it catalyzes nanoparticle formation through catechol redox cycling to semiquinones and/or ortho-benzoquinones.

Appreciating the iron regulatory mechanisms used with these dual-functioning metallophores is useful for understanding their action within their own environmental context. Microbes have evolved regulatory mechanisms to produce metallophores or siderophores when metal concentrations are low. Iron regulatory mechanisms for siderophores are well understood, where low iron concentrations drive the production of siderophores to sequester iron for biological processes where production is slowed after required iron concentrations have been met (Hider & Kong, 2010; Varma & Chincholkar, 2007). For D. acidovorans, the environmental context is one of high gold and low iron concentration where delftibactin production is additionally driven for need of iron (Johnston et al., 2013; Reith et al., 2010). It is therefore useful to gain insight into the ability of dual-functioning metallophores (delftibactin and enterobactin) to generate gold nanoparticles in the presence of iron. If delftibactin A is pre-exposed to iron, its gold reducing power is reduced (FIG. 24c). This is due to the chelation core being directly involved in coordinating the reduction of $Au^{3+}$ to $Au^0$ nanoparticles. Enterobactin was also examined for its reactivity with gold both in the presence of iron (FIG. 24c) and after being pre-reacted with iron (FIG. 24d) to determine whether initial complexation of $Au^{3+}$ by its chelation core is also responsible for gold nanoparticle formation. In this reaction, enterobactin reacts with gold to a similar extent as when iron is not present. This suggests the mechanism of gold nanoparticle formation caused by enterobactin is through catechol mediated redox chemistry and does not require binding of $Au^{3+}$ within its chelation core to reduce $Au^{3+}$ to gold nanoparticles. This is different from delftibactin A, where $Au^{3+}$ interacts with N-hydroxy ornithine within the chelation core and is required for gold nanoparticle formation, giving evidence that delftibactin A (and B) is a more suited to metallophore-mediated protection from gold toxicity within the environment that D. acidovorans is found.

CONCLUSION

Although it has been demonstrated that other metallophores are capable of reducing trivalent gold to form gold nanoparticles, the unique sacrificial mechanism observed during gold nanoparticle formation by the delftibactins provides an advantage in its unique environmental niche. These protective molecules have helped D. acidovorans establish itself as one of two predominant gold resident bacteria, and has facilitated the development of bacterioform gold deposits through small molecule mediated biomineralization. Taking advantage of the properties of delftibactins and related microbial metallophores can lead to biotechnological approaches for the detection and extraction of gold.

While the present disclosure has been described with reference to what are presently considered to be the examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Adenylation domain specificities. Prediction of incorporated amino acids was performed using NRPSPredictor and NRPS PKS, providing a probability sequence for the NRPS/PKS product

| Adenylation Domain | Active Site Residues | Substrate | Product |
|---|---|---|---|
| DelE A1 | DMGGYGCLFK<br>DAGGCAMVAK | Alanine<br>Alanine | HC Toxin |
| DelE A2 | DIWHISLIEK<br>DVWHISLIDK | Inactive<br>Serine | Nostopeptolide |
| DelG A1 | DLTKVCHVGK<br>DLTKVGHIGK | Aspartic acid<br>Aspartic acid | Surfactin |
| DelG A2 | DFWNIGMVHK<br>DFWNIGMVHK | Threonine<br>Threonine | Syringopeptin |
| DelG A3 | DILQLGLIWK<br>DILQLGLIWK | Glycine<br>Glycine | Nostopeptolide |
| DelH A1 | DFWNIGMVHK<br>DFWNIGMVHK | Threonine<br>Threonine | Syringopeptin |
| DelH A2 | DVWNIGLIHK<br>DVGEIGSIDK | Ornithine<br>Ornithine | Fengycin |
| DelH A3 | DVWHLSLIDK<br>DVWHLSLIDK | Serine<br>Serine | Syringopeptin |
| DelH A4 | DGEDHGAVTK<br>DAEDIGAITK | Arginine<br>Arginine | Pederin |
| DelH A5 | DGEAVGGVTK<br>DGESSGGMTK | $N^{\delta}$-hydroxyornithine<br>$N^{\delta}$-hydroxyornithine | Vicibactin |

TABLE 2

Primers used in construction of the ΔdelG strain

| PCR Primer | Sequence (5'-3') | Purpose |
|---|---|---|
| TetNotF | TTT TGC GGC CGC TGC TGA ACC CCC AA | Amplification of tetracycline resistance cassette from pLLX13. |
| TetNotR | TTT TGC GGC CGC TAT CGT TTC CAC GA | Amplification of the tetracycline resistance cassette from pLLX13. |
| 2kbNRPS2Xba2 | TTT TTC TAG ACG CAT TGC TGA ACT ACC | Amplification of the 2 kb delG fragment from D. acidavorans. |
| 2kbNRPS2Sac2 | TTT TGA GCT CAG CAG TTG CAC CAC CT | Amplification of the 2 kb delG fragment from D. acidavorans. |
| OriTF | TTT TAA GCT TTT CCT CAA TCG CTC TTC | Amplification of an oriT from pLLX13. |
| OriTR | TTT TAA GCT TTT TTC GCA CGA TAT ACA | Amplification of an oriT from pLLX13. |

TABLE 2 - continued

Primers used in construction of the ΔdelG strain

| PCR Primer | Sequence (5'-3') | Purpose |
|---|---|---|
| NRPS2Seq2 | GGG GTG CGG AAA ATG TCC TG | Confirmation of genomic integration of the tetracycline resistance cassette. |

TABLE 3

Delftibactin production in response to [$Fe^{3+}$]

| Media [Iron] | [Delftibactin] |
|---|---|
| 0 | 205.8 ± 28.0 μM |
| 100 nM | 196.1 ± 30.7 μM |
| 1 μM | 149.3 ± 21.0 μM |
| 10 μM | 21 ± 9.4 μM |
| 100 μM | 2.2 ± 1.4 μM |
| 1 mM | Growth Inhibitory |

TABLE 4

| Locus | Gene | Predicted Function | Strand | Amino Acids |
|---|---|---|---|---|
| Daci_4765 | — | Heavy metal efflux outer membrane component | − | 485 |
| Daci_4764 | — | Heavy metal efflux periplasmic component | − | 405 |
| Daci_4763 | — | Heavy metal efflux inner membrane component | − | 1029 |
| Daci_4762 | — | Nitrogen regulatory protein P-II | − | 111 |
| Daci_4761 | — | RNA polymerase, sigma subunit | − | 174 |
| Daci_4760 | delA | MbtH domain protein | − | 121 |
| Daci_4759 | delB | Thioesterase | − | 247 |
| Daci_4758 | delC | Phosphopantetheinyl transferase | − | 229 |
| Daci_4757 | delD | Aspartic acid dioxygenase | − | 329 |
| Daci_4756 | delE | Nonribosomal peptide synthetase | − | 1789 |
| Daci_4755 | delF | Polyketide synthase | − | 1560 |
| Daci_4754 | delG | Nonribosomal peptide synthetase | − | 3331 |
| Daci_4753 | delH | Nonribosomal peptide synthetase | − | 6176 |
| Daci_4752 | delI | Siderophore receptor | − | 799 |
| Daci_4751 | delJ | anti-FecI sigma factor, FecR | + | 344 |
| Daci_4750 | delK | RNA polymerase, sigma subunit | + | 199 |
| Daci_4749 | delL | Lysine/Ornithine N-monooxygenase | + | 432 |
| Daci_4748 | delM | Acetyltransferase | + | 400 |
| Daci_4747 | delN | Esterase/Lipase | + | 321 |
| Daci_4746 | delO | Siderophore Export Pump | + | 571 |
| Daci_4745 | delP | N5-hydroxyornithine formyltransferase | − | 284 |

REFERENCES

Amin, S. A., et al. *J. Am. Chem. Soc.* 129, 478-479 (2007).
Ansari, M. Z., Yadav, G., Gokhale, R. S. and Mohanty, D. *Nucleic Acids Res.* 32, W405-413 (2004).
Berner, I., Greiner, M., Metzger, J., Jung, G., Winkelmann, G. 1991. Identification of Enterobactin and Linear Dihydroxybenzoylserine Compounds by Hplc and Ion Spray Mass-Spectrometry (Lc/Ms and Ms/Ms). *Biol, Met.,* 4(2), 113-118.
Chaturvedi, K. S., et al. *Nat. Chem. Bio.* 8, 731-736 (2012).
Diels, L., Dong, Q., van der Lelie, D., Baeyens, W. and Mergeay, M. *J. Ind. Microbiol. Biot.* 14, 142-153 (1995).
Drummond, A. J., et al. *Geneious* v4.7 (2009).
Henderson, J. P., Crowley, J. R., Pinkner, J. S., Walker, J. N., Tsukayama, P., Stamm, W. E., Hooton, T. M., Hultgren, S.

J. 2009. Quantitative Metabolomics Reveals an Epigenetic Blueprint for Iron Acquisition in Uropathogenic *Escherichia coli*. *Plos Pathog.*, 5(2).
Hider, R. C. and Kong, X. *Nat. Prod. Rep.* 27, 637-57 (2010).
Hough, R. M., et al. *Geology* 36, 571-574 (2008).
Kashefi, K., Tor, J. M., Nevin, K. P. and Lovely, D. R. *Appl. Env. Microbiology* 67, 3275-3279 (2001).
Johnston, C. W., Wyatt, M. A., Li, X., Ibrahim, A., Shuster, J., Southam, G., Magarvey, N. A. 2013. Gold biomineralization by a metallophore from a gold-associated microbe. *Nat. Chem. Biol.*, 9(4), 241-3.
Kim, H. J., et al. *Science* 305, 1612-1615 (2004).
Lengke, M., Sanpawanitchakit, C., Southam, G. 2011. Biosynthesis of Gold Nanoparticles: A Review. in: *Met. Nanopart. Microbiol.*, (Eds.) M. Rai, N. Duran, Springer Berlin Heidelberg, pp. 37-74.
Lin, H., Fiscchbach, M. A., Liu, D. R., Walsh, C. T. 2005. In vitro characterization of salmochelin and enterobactin trilactone hydrolases IroD, IroE, and Fes. *J. Am. Chem. Soc.*, 127(31), 11075-11084.
Malhotra, A., Dolma, K., Kaur, N., Rathore, Y. S., Ashish, Mayilraj, S., Choudhury, A. R. 2013. Biosynthesis of gold and silver nanoparticles using a novel marine strain of Stenotrophomonas. *Biores. Technol*, 142(0), 727-731.
Miller, M. C., et al. *Microbiology* 156, 2226-38 (2010).
Nies, D. H. Appl. *Microbiol. Biotechnol.* 51, 730-750 (1999).
Ojea-Jiménez, I., Romero, F. M., Bastús, N. G. and Puntes, V. *J. Phys. Chem.* 114, 1800-1804 (2010).
Pinel, N., Davidson, S. K. and Stahl, D. A. *IJSEM* 58, 2147-2157 (2008).
Rausch, C., Weber, T., Kohlbacher, O., Wohlleben, W. and Huson, D. H. *Nucleic Acids Res.* 33, 5799-5808 (2005).
Reith, F., et al. *Geology* 38, 843-846 (2010).
Reith, F., et al. *Proc. Natl Acad. Sci. USA* 106, 17757-17762 (2009).
Reith, F., Lengke, M. F., Falconer, D., Craw, D. and Southam, G. *The ISME Journal* 1, 567-584 (2007).
Reith, F., Rogers, S. L., McPhail, D. C. and Webb, D. *Science* 313, 233-236 (2006).
Salem, I. B., et al. *Ann. Microbiol.*, 1-12 (2012).
Schweigert, N., Zehnder, A. J. B., Eggen, R. I. L. 2001. Chemical properties of catechols and their molecular modes of toxic action in cells, from microorganisms to mammals. *Environ. Microbiol.*, 3(2), 81-91.
Stachelhaus, T., Mootz, H. D. and Marahiel, M. A. *Chemistry & Biology* 6, 493-505 (1999).
Usher, A., McPhail, D. C. and Brugger, J. *Geochim. Cosmochim. Acta* 73, 3359-3380 (2009).
Valdebenito, M., Crumbliss, A. L., Winkelmann, G., Hantke, K. 2006. Environmental factors influence the production of enterobactin, salmochelin, aerobactin, and yersiniabactin in *Escherichia coli* strain Nissle 1917. *Int. J. Med. Microbiol.*, 296(8), 513-20.
Varma, A., Chincholkar, S. B. 2007. *Microbial siderophores*. Springer Verlag.
Vining, L. C. *Annu. Rev. Microbiol.* 44, 395-427 (1990).
Weisburg, W. G., Barns, S. M., Pelletier, D. A. and Lane, D. J. *J. Bacteriol.* 173, 697-703 (1991).

The invention claimed is:
1. A method of removing soluble gold in a sample comprising:
   (a) contacting the sample with a metallophore under conditions which convert the soluble gold into solid gold; and
   (b) isolating the solid gold from the sample,
wherein the metallophore is a microbial metabolite which converts the soluble gold to solid gold ($Au^0$) selected from one or more of:

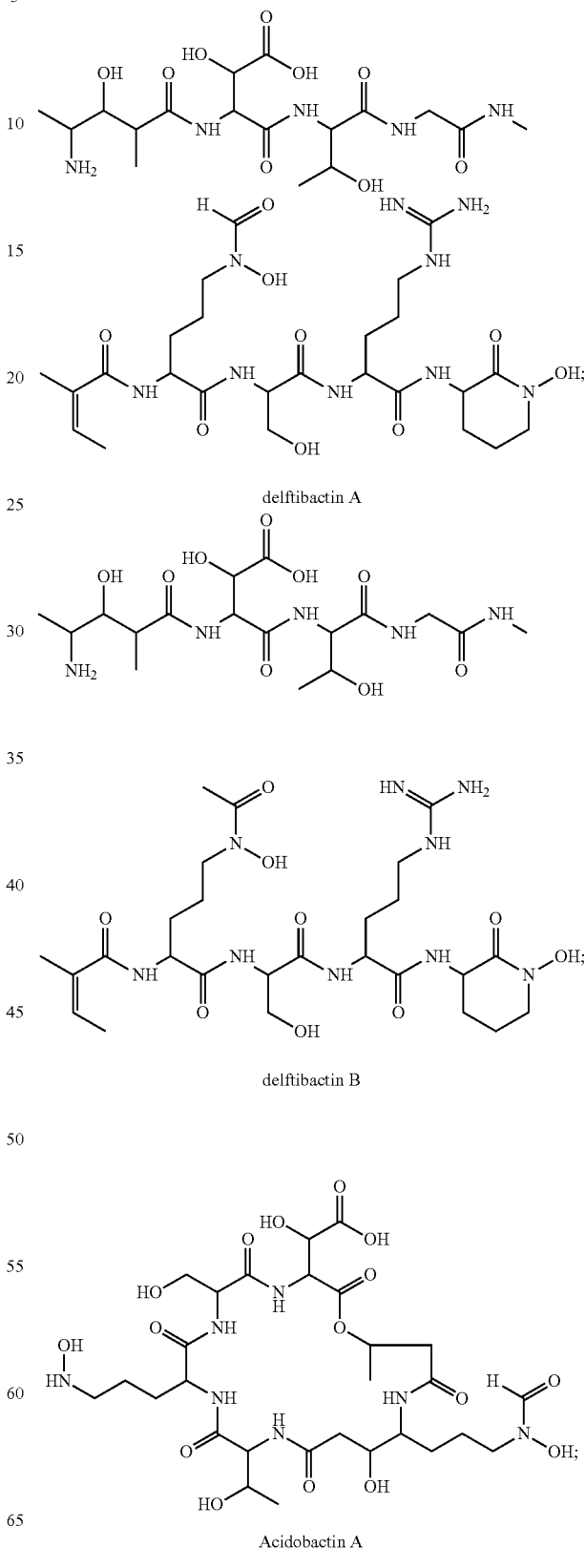

delftibactin A delftibactin B

Acidobactin A

-continued
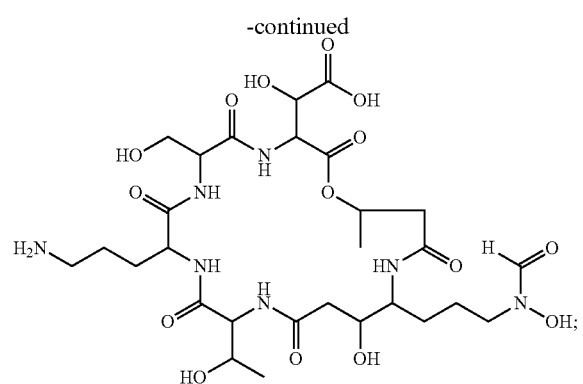
Acidobactin B
Vacidobactin A
Vacidobactin B
and a compound of Formula III:
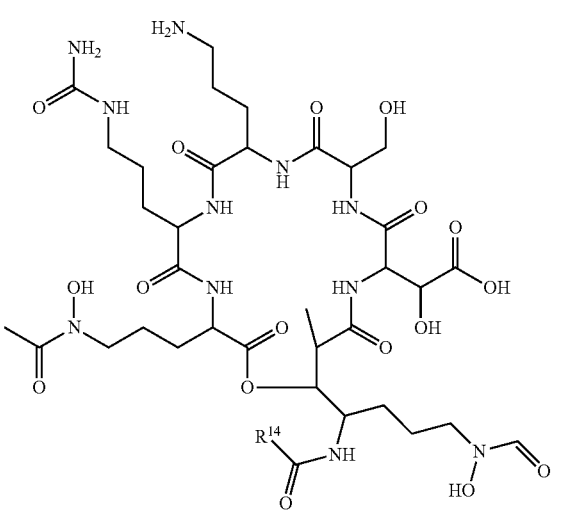
(III)
wherein $R^{14}$ is selected from $C_{8-16}$alkyl and $C_{8-16}$alkenyl,
or a salt of any of the above.
2. The method of claim 1, wherein the metallophore is delftibactin A:
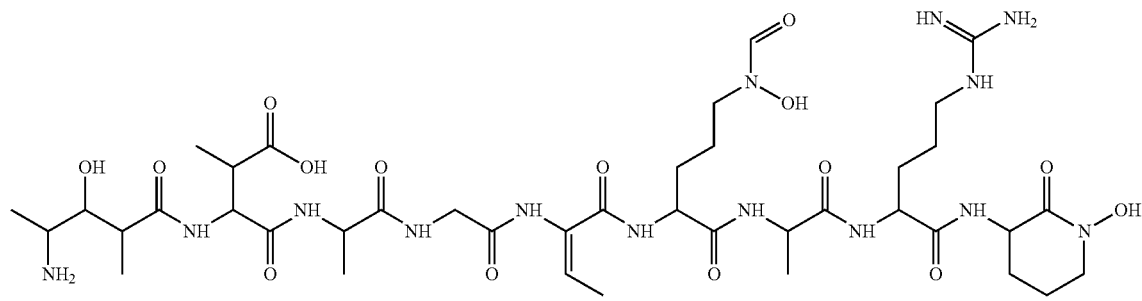 [SMILES: C/C=C(/NC(=O)CNC(=O)C(C)NC(=O)C(NC(=O)C(C)C(O)C(C)N)C(C)C(=O)O)C(=O)NC(CCCN(O)C=O)C(=O)NC(C)C(=O)NC(CCCNC(=N)N)C(=O)NC1CCCN(O)C1=O]

or delftibactin B:

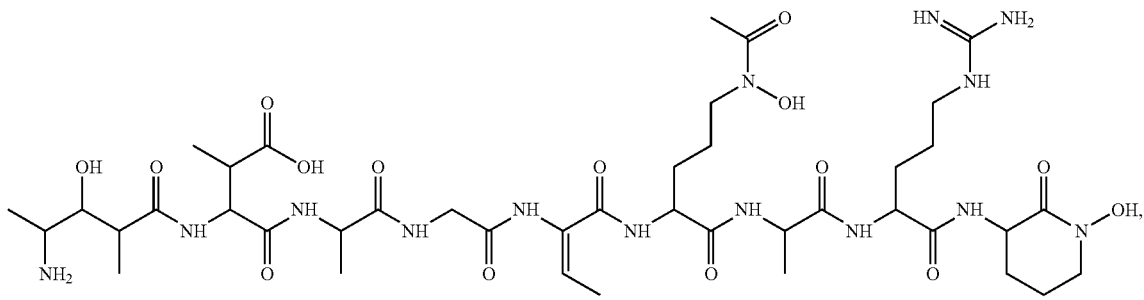 [SMILES: C/C=C(/NC(=O)CNC(=O)C(C)NC(=O)C(NC(=O)C(C)C(O)C(C)N)C(C)C(=O)O)C(=O)NC(CCCN(O)C(C)=O)C(=O)NC(C)C(=O)NC(CCCNC(=N)N)C(=O)NC1CCCN(O)C1=O]

or a salt thereof, or a combination thereof.

3. The method of claim 2, wherein the metallophore is delftibactin A or a salt thereof.

4. The method of claim 2, wherein the metallophore is delftibactin B or a salt thereof.

5. The method of claim 2, wherein the metallophore is a combination of delftibactin A and delftibactin B, and/or salts thereof.

6. The method of claim 1, wherein the conditions for contacting of the sample with the metallophore comprise mixing the sample and the metallophore in solution at ambient temperature for a time sufficient for the formation of solid gold and, optionally, pretreating the sample to liberate soluble gold ions for binding to the metallophore.

7. The method of claim 6, wherein the formation of the solid gold is detected by observing formation of a dark precipitate which is observed using colormetric detection or visually.

8. The method of claim 7, wherein the dark precipitate is observed using colormetric detection.

9. The method of claim 6, wherein the sample is pretreated to liberate the soluble gold ions.

10. The method of claim 9, wherein the sample is pretreated with acid solutions to liberate the soluble gold ions.

11. The method of claim 1, wherein the solid gold that is formed is gold nanoparticles.

12. The method of claim 1, wherein one, two or three, different metallophores are used.

13. The method of claim 1, wherein the isolation of the solid gold is by centrifugation or filtration.

14. The method of claim 1, wherein the soluble gold is a gold ion.

15. The method of claim 14, wherein the soluble gold is $Au^{3+}$.

16. The method of claim 1, wherein the sample is a liquid solution.

17. The method of claim 16, wherein the sample is an environmental sample where the presence of toxic soluble gold is undesirable.

18. The method of claim 1, wherein the sample does not comprise iron.

19. The method of claim 1, wherein the metallophore is selected from one or more of:

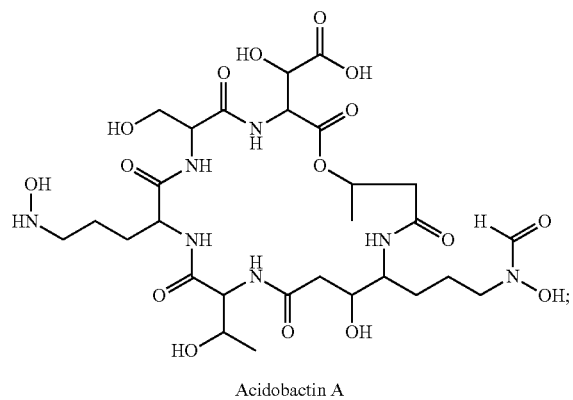

Acidobactin A

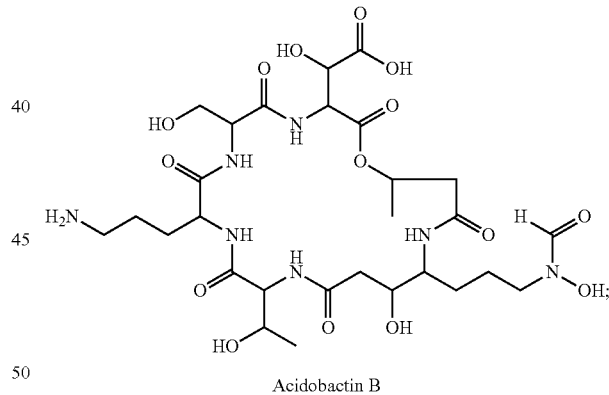

Acidobactin B

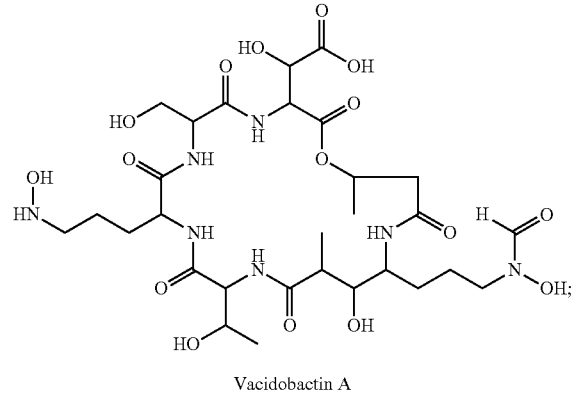

Vacidobactin A

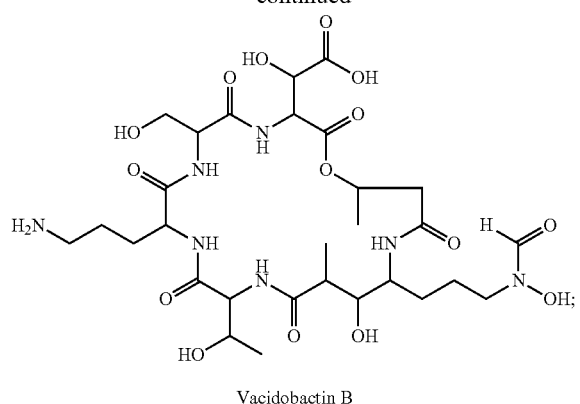
Vacidobactin B
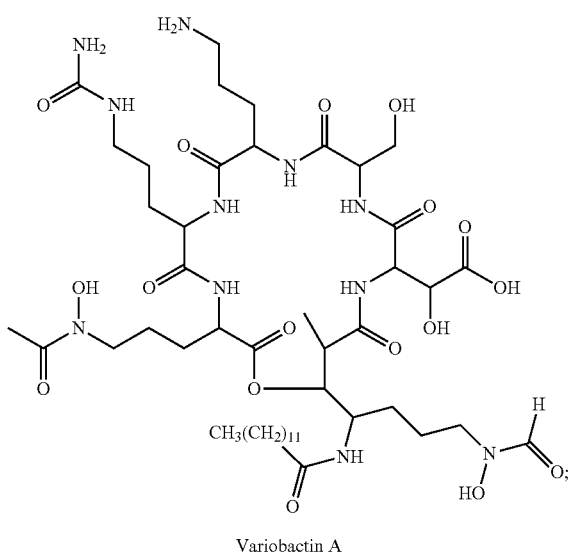
Variobactin A
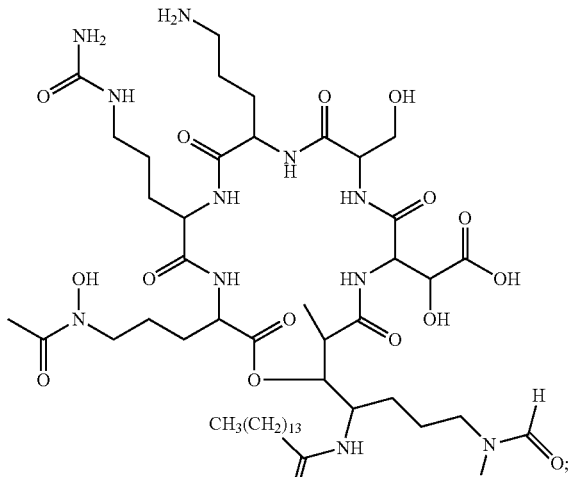
Variobactin B
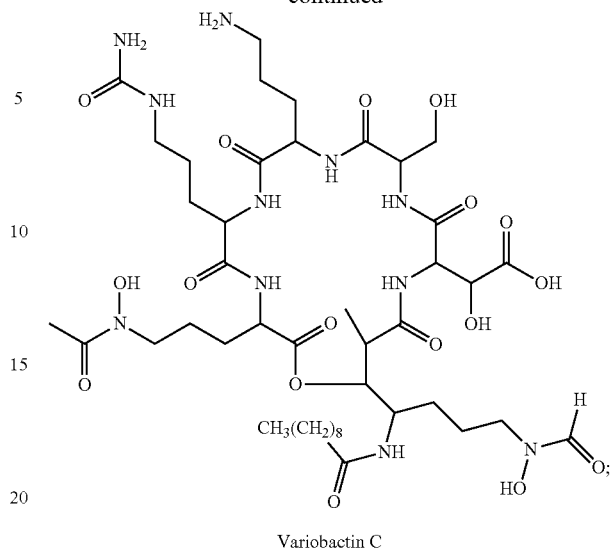
Variobactin C
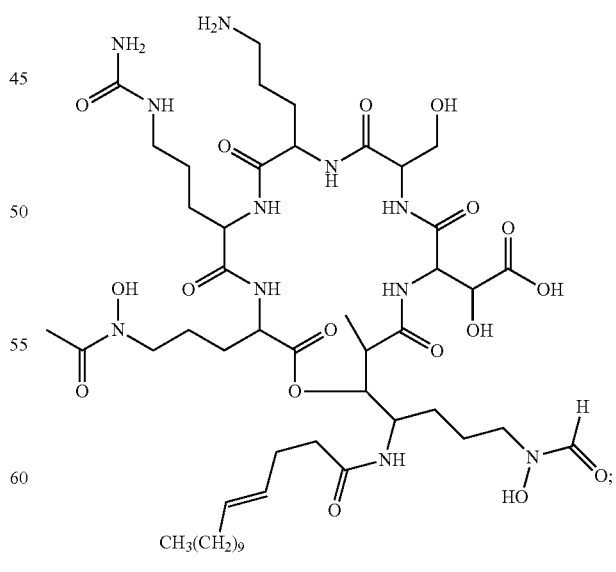
Variobactin D
and

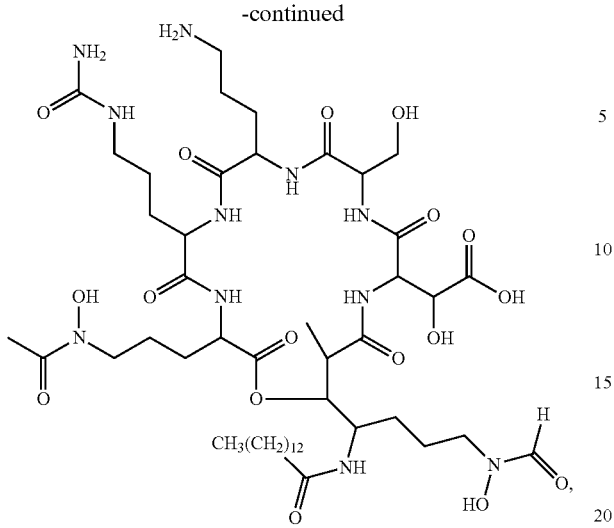
Variobactin E
or a salt of any of the above.
* * * * *

UNITED STATES PATENT AND TRADEMARK OFFICE
CERTIFICATE OF CORRECTION

Page 1 of 5

PATENT NO. : 10,174,401 B2
APPLICATION NO. : 14/760527
DATED : January 8, 2019
INVENTOR(S) : Morgan Wyatt et al.

It is certified that error appears in the above-identified patent and that said Letters Patent is hereby corrected as shown below:

In the Drawings

Figure 4:
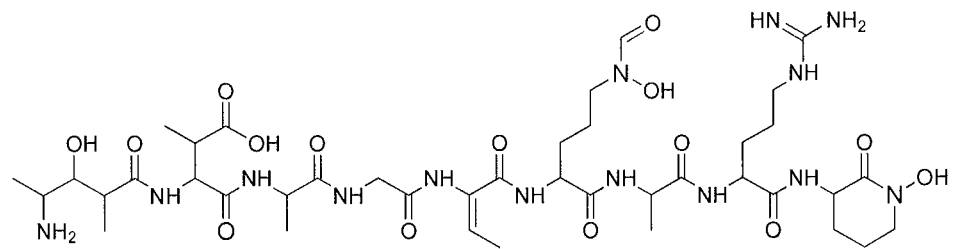
FIG. 4 shows the structure of the gold interacting non-ribosomal peptide delftibactin A as one exemplary embodiment of the present application.

1. Figure 4 should read as shown on the attached drawing sheet.

In the Specification

2. Column 13, Line 30, should read as follows:

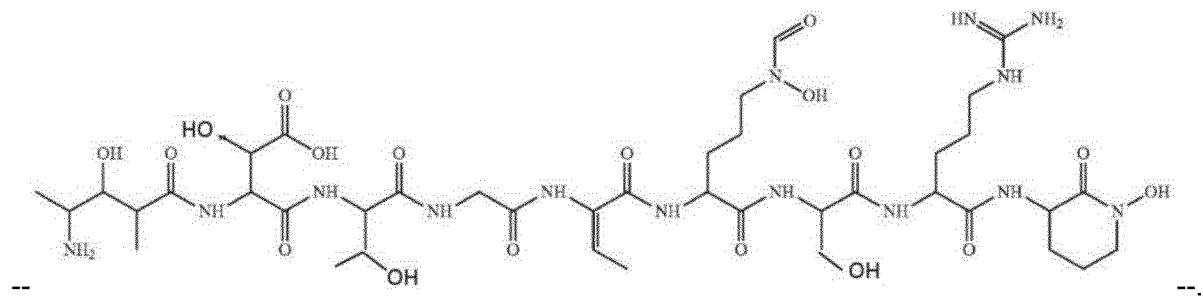

3. Column 13, Line 50, should read as follows:

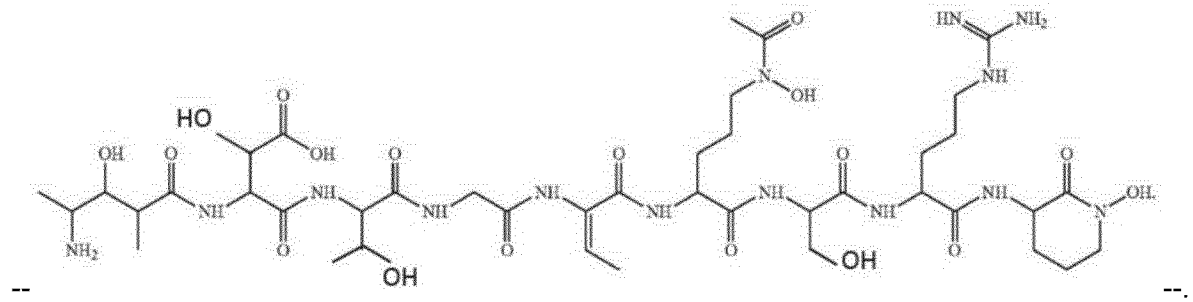

Signed and Sealed this
Seventeenth Day of September, 2019

Andrei Iancu
*Director of the United States Patent and Trademark Office*

4. Column 19, Line 1, should read as follows:
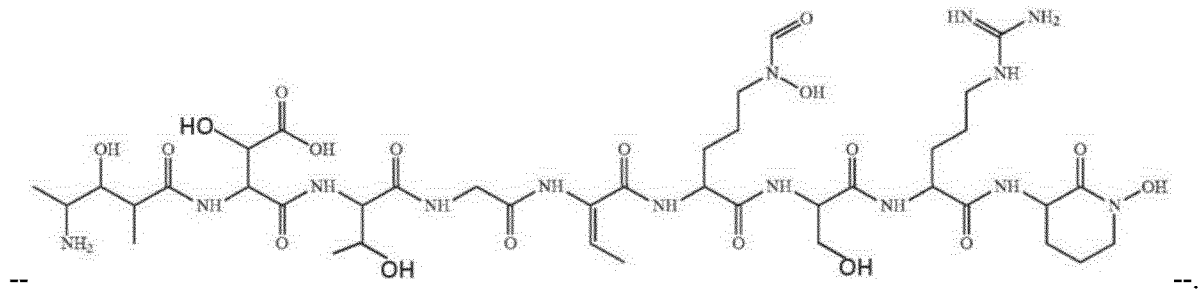
--                                                                                 --.
5. Column 19, Line 20, should read as follows:
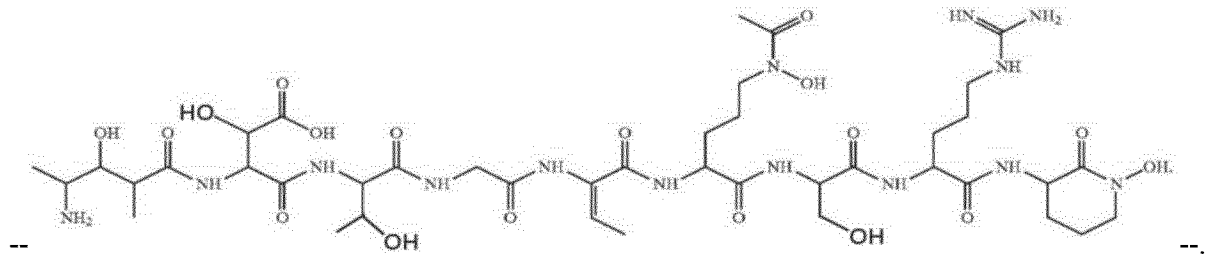
--                                                                                 --.
6. Column 40, Line 6, should read as follows:
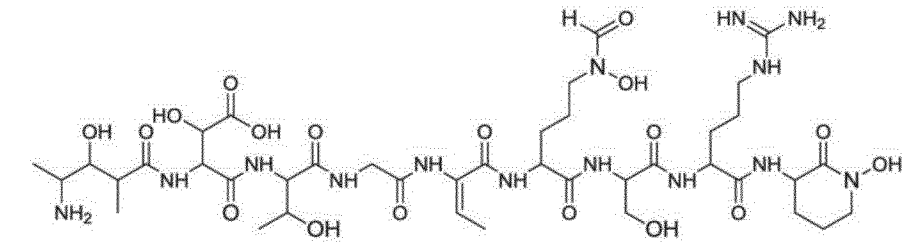
--                    delftibactin A;                    --.
7. Column 40, Line 36, should read as follows:
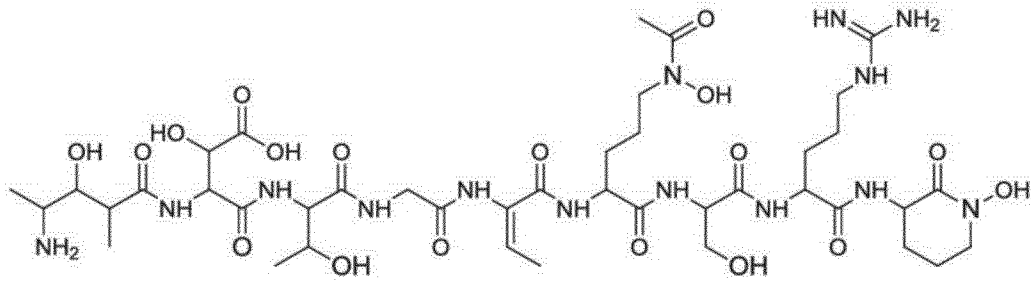
--                    delftibactin B;                    --.
8. Column 40, Line 67, "Acidobactin A" should read --Acidobactin A;--.
9. Column 41, Line 16, "Acidobactin B" should read --Acidobactin B;--.

CERTIFICATE OF CORRECTION (continued)
U.S. Pat. No. 10,174,401 B2

Page 3 of 5

10. Column 41, Line 31, "Vacidobactin A" should read --Vacidobactin A;--.

11. Column 41, Line 48, "Vacidobactin B" should read --Vacidobactin B;--.

12. Column 42, Line 15, should read as follows:

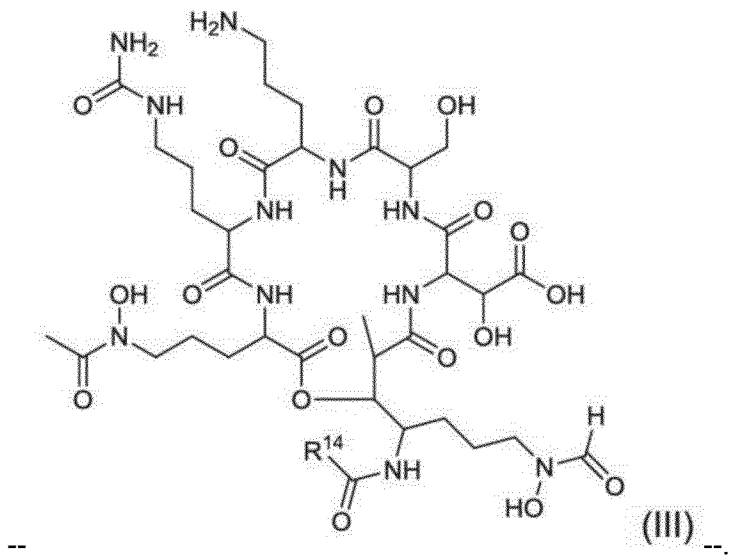

--.

13. Column 42, Line 52, should read as follows:

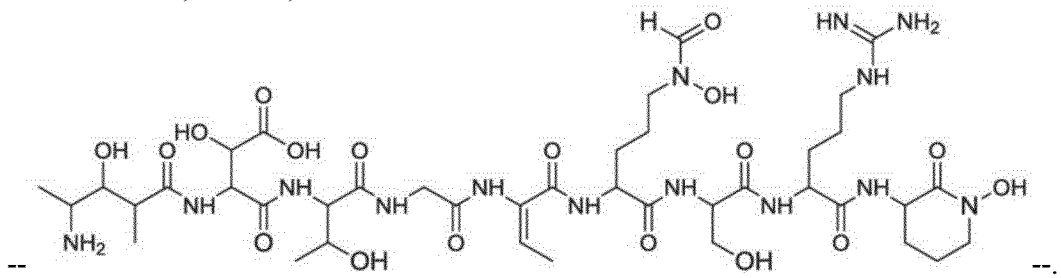

--.

14. Column 43, Line 5, should read as follows:

or delftibactin B:

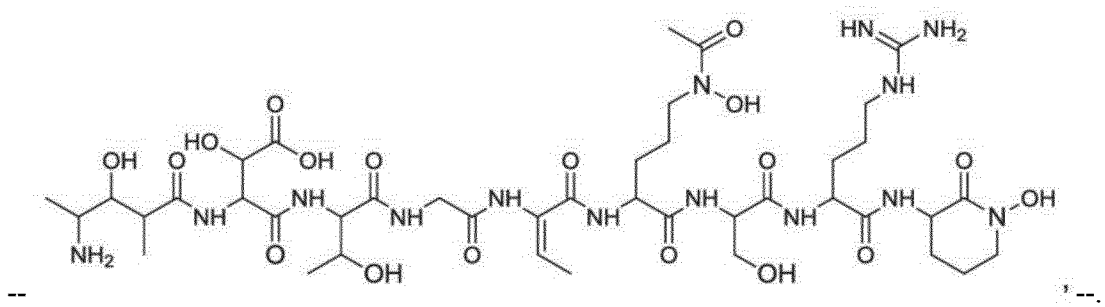

--.

CERTIFICATE OF CORRECTION (continued)
U.S. Pat. No. 10,174,401 B2

15. Column 43, Line 62, "environmental sample where the presence of toxic soluble gold is undesirable" should read --environmental sample.--.

16. Column 44, Line 33, "Acidobactin A" should read --Acidobactin A;--.

17. Column 44, Line 51, "Acidobactin B" should read --Acidobactin B;--.

18. Column 44, Line 66, "Vacidobactin A" should read --Vacidobactin A;--.

19. Column 45, Line 17, "Vacidobactin B" should read --Vacidobactin B;--.

20. Column 45, Line 41, "Variobactin A" should read --Variobactin A;--.

21. Column 45, Line 66, "Variobactin B" should read --Variobactin B;--.

22. Column 46, Line 22, "Variobactin C" should read --Variobactin C;--.

23. Column 46, Line 64, should read as follows:
--Variobactin D; and--.

24. Column 47, Line 23, "Variobactin E" should read --Variobactin E;--.